(12) United States Patent
Chin

(10) Patent No.: US 7,955,355 B2
(45) Date of Patent: Jun. 7, 2011

(54) METHODS AND DEVICES FOR IMPROVING PERCUTANEOUS ACCESS IN MINIMALLY INVASIVE SURGERIES

(75) Inventor: Kingsley R. Chin, Philadelphia, PA (US)

(73) Assignee: Stryker Spine (FR)

( * ) Notice: Subject to any disclaimer, the term of this patent is extended or adjusted under 35 U.S.C. 154(b) by 957 days.

(21) Appl. No.: 10/868,075

(22) Filed: Jun. 15, 2004

(65) Prior Publication Data

US 2005/0065517 A1 Mar. 24, 2005

Related U.S. Application Data

(63) Continuation-in-part of application No. 10/669,927, filed on Sep. 24, 2003, now Pat. No. 7,282,064.

(60) Provisional application No. 60/518,580, filed on Nov. 8, 2003.

(51) Int. Cl.
*A61B 17/70* (2006.01)
(52) U.S. Cl. .................................................. 606/246
(58) Field of Classification Search .................... 606/61, 606/99, 246
See application file for complete search history.

(56) References Cited

U.S. PATENT DOCUMENTS

| | | | |
|---|---|---|---|
| 3,788,318 A | 1/1974 | Kim et al. |
| 3,789,852 A | 2/1974 | Kim |
| 3,892,232 A | 7/1975 | Neufeld |
| 4,269,184 A | 5/1981 | Montgomery |
| 4,350,151 A | 9/1982 | Scott |
| 4,409,968 A | 10/1983 | Drummond |
| 4,411,259 A | 10/1983 | Drummond |
| 4,448,191 A | 5/1984 | Rodnyansky et al. |
| 4,449,532 A | 5/1984 | Storz et al. |
| 4,545,374 A | 10/1985 | Jacobson |
| 4,562,832 A | 1/1986 | Wilder |
| 4,611,581 A | 9/1986 | Steffee |
| 4,790,297 A | 12/1988 | Luque |

(Continued)

FOREIGN PATENT DOCUMENTS

DE 19726754 2/1999

(Continued)

OTHER PUBLICATIONS

CD Horizon SEXTANT, Marketing Brochure, Medtronic Sofamor Danek USA, Inc., Memphis TN 38132.

(Continued)

*Primary Examiner* — Nicholas Woodall
(74) *Attorney, Agent, or Firm* — Lerner, David, Littenberg, Krumholz & Mentlik, LLP

(57) ABSTRACT

A device for use as a portal in percutaneous minimally invasive surgery performed within a patient's body cavity includes a first elongated hollow tube having a length adjusted with a self-contained mechanism. The first elongated tube includes an inner hollow tube and an outer hollow tube and the inner tube is adapted to slide within the outer tube thereby providing the self-contained length adjusting mechanism. This length-adjustment feature is advantageous for percutaneous access surgery in any body cavity. Two or more elongated tubes with adjustable lengths can be placed into two or more adjacent body cavities, respectively. Paths are opened within the tissue areas between the two or more body cavities, and are used to transfer devices and tools between the adjacent body cavities. This system of two or more elongated tubes with adjustable lengths is particularly advantageous in percutaneous minimally invasive spinal surgeries, and provides the benefits of minimizing long incisions, recovery time and post-operative complications.

23 Claims, 22 Drawing Sheets

U.S. PATENT DOCUMENTS

| | | |
|---|---|---|
| 4,817,587 A | 4/1989 | Janese |
| 4,862,891 A | 9/1989 | Smith |
| 4,899,729 A | 2/1990 | Gill |
| 4,913,134 A | 4/1990 | Luque |
| 4,984,564 A | 1/1991 | Yuen |
| 5,010,879 A | 4/1991 | Moriya et al. |
| 5,027,793 A | 7/1991 | Engelhardt et al. |
| 5,035,232 A | 7/1991 | Lutze |
| 5,125,396 A | 6/1992 | Ray |
| 5,139,487 A | 8/1992 | Baber |
| 5,171,279 A | 12/1992 | Mathews |
| 5,183,464 A | 2/1993 | Dubrul et al. |
| 5,195,541 A | 3/1993 | Obenchain |
| 5,197,971 A | 3/1993 | Bonutti |
| 5,242,443 A | 9/1993 | Kambin |
| 5,293,863 A | 3/1994 | Zhu et al. |
| 5,295,994 A | 3/1994 | Bonutti |
| D346,217 S | 4/1994 | Sparker et al. |
| 5,312,417 A | 5/1994 | Wilk |
| 5,357,983 A | 10/1994 | Mathews |
| 5,377,667 A | 1/1995 | Patton |
| 5,381,788 A | 1/1995 | Matula |
| 5,395,317 A | 3/1995 | Kambin |
| 5,409,488 A | 4/1995 | Ulrich |
| 5,425,732 A | 6/1995 | Ulrich |
| 5,439,464 A | 8/1995 | Shapiro |
| 5,454,365 A | 10/1995 | Bonutti |
| 5,464,011 A | 11/1995 | Bridge |
| 5,480,440 A | 1/1996 | Kambin |
| 5,496,322 A | 3/1996 | Mathews |
| 5,545,228 A | 8/1996 | Kambin |
| 5,569,248 A | 10/1996 | Mathews |
| 5,569,290 A | 10/1996 | McAfee |
| 5,584,887 A | 12/1996 | Kambin |
| 5,601,562 A | 2/1997 | Wolf et al. |
| 5,601,590 A | 2/1997 | Bonutti |
| 5,707,359 A | 1/1998 | Bufalini |
| 5,720,751 A | 2/1998 | Jackson |
| 5,728,097 A | 3/1998 | Mathews |
| 5,741,261 A | 4/1998 | Moskovitz |
| 5,743,907 A | 4/1998 | Asher et al. |
| 5,746,720 A | 5/1998 | Stouder, Jr. |
| 5,762,629 A | 6/1998 | Kambin |
| 5,772,594 A | 6/1998 | Barrick |
| 5,792,044 A | 8/1998 | Foley et al. |
| 5,795,289 A | 8/1998 | Wyttenbach |
| 5,882,344 A | 3/1999 | Stouder, Jr. |
| 5,885,291 A | 3/1999 | Moskovitz |
| 5,885,292 A | 3/1999 | Moskovitz |
| 5,891,147 A | 4/1999 | Moskovitz |
| 5,902,231 A | 5/1999 | Foley |
| 5,928,139 A | 7/1999 | Koros et al. |
| 5,944,658 A | 8/1999 | Koros et al. |
| 5,954,635 A | 9/1999 | Foley |
| 5,957,888 A | 9/1999 | Hinchliffe |
| 5,961,499 A | 10/1999 | Bonutti |
| 5,964,761 A | 10/1999 | Kambin |
| 5,976,146 A | 11/1999 | Ogawa et al. |
| 6,007,487 A | 12/1999 | Foley |
| 6,033,406 A | 3/2000 | Mathews |
| 6,036,692 A | 3/2000 | Burel et al. |
| 6,080,156 A | 6/2000 | Asher |
| 6,127,597 A | 10/2000 | Beyar |
| 6,152,871 A | 11/2000 | Foley |
| 6,159,179 A | 12/2000 | Simonson |
| 6,162,170 A | 12/2000 | Foley |
| 6,175,758 B1 | 1/2001 | Kambin |
| 6,176,823 B1 | 1/2001 | Foley et al. |
| 6,183,472 B1 | 2/2001 | Lutz |
| 6,187,000 B1 | 2/2001 | Davison |
| 6,197,002 B1 | 3/2001 | Peterson |
| 6,200,322 B1 | 3/2001 | Branch |
| 6,206,822 B1 | 3/2001 | Foley et al. |
| 6,206,826 B1 | 3/2001 | Mathews |
| 6,217,509 B1 | 4/2001 | Foley |
| 6,226,548 B1 | 5/2001 | Foley et al. |
| 6,235,028 B1 | 5/2001 | Brumfield et al. |
| 6,287,313 B1 | 9/2001 | Sasso |
| 6,338,730 B1 | 1/2002 | Bonutti |
| 6,358,266 B1 | 3/2002 | Bonutti |
| 6,371,968 B1 | 4/2002 | Kogasaka |
| 6,425,859 B1 | 7/2002 | Foley |
| 6,485,518 B1 | 11/2002 | Cornwall |
| 6,506,151 B2 | 1/2003 | Estes |
| 6,520,907 B1 | 2/2003 | Foley et al. |
| 6,524,320 B2 | 2/2003 | DiPoto |
| 6,530,926 B1 | 3/2003 | Davison |
| 6,530,929 B1 | 3/2003 | Justis |
| 6,558,386 B1 | 5/2003 | Cragg |
| 6,558,390 B2 | 5/2003 | Cragg |
| 6,562,046 B2 | 5/2003 | Sasso |
| 6,575,979 B1 | 6/2003 | Cragg |
| 6,596,008 B1 | 7/2003 | Kambin |
| 6,605,095 B2 | 8/2003 | Grossman |
| 6,607,530 B1 | 8/2003 | Carl et al. |
| 6,613,050 B1 | 9/2003 | Wagner |
| 6,652,553 B2 | 11/2003 | Davison |
| 6,692,434 B2 | 2/2004 | Ritland |
| 6,692,473 B2 | 2/2004 | St. Cyr |
| 6,723,095 B2 | 4/2004 | Hammerslag |
| 6,740,089 B2 | 5/2004 | Haider |
| 6,740,090 B1 | 5/2004 | Cragg |
| 6,746,449 B2 | 6/2004 | Jones et al. |
| 6,749,614 B2 | 6/2004 | Teitelbaum |
| 6,770,074 B2 | 8/2004 | Michelson |
| 6,790,210 B1 | 9/2004 | Cragg |
| 6,793,656 B1 | 9/2004 | Mathews |
| 6,800,084 B2 | 10/2004 | Davison |
| 6,811,558 B2 | 11/2004 | Davison |
| 6,821,277 B2 | 11/2004 | Teitelbaum |
| 6,837,891 B2 | 1/2005 | Davison |
| 6,849,064 B2 | 2/2005 | Hamada |
| 6,923,811 B1 | 8/2005 | Carl et al. |
| 6,929,647 B2 * | 8/2005 | Cohen ............... 606/99 |
| 7,011,660 B2 | 3/2006 | Sherman et al. |
| 7,083,621 B2 | 8/2006 | Shaolian et al. |
| 7,160,300 B2 * | 1/2007 | Jackson ............ 606/61 |
| 7,250,052 B2 * | 7/2007 | Landry et al. ...... 606/61 |
| 7,306,603 B2 * | 12/2007 | Boehm et al. ...... 606/61 |
| 2001/0011170 A1 | 8/2001 | Davison et al. |
| 2001/0027320 A1 | 10/2001 | Sasso |
| 2001/0029353 A1 | 10/2001 | Peterson |
| 2001/0049498 A1 | 12/2001 | Davison et al. |
| 2001/0049527 A1 | 12/2001 | Cragg |
| 2001/0053915 A1 | 12/2001 | Grossman |
| 2002/0016583 A1 | 2/2002 | Cragg |
| 2002/0045904 A1 | 4/2002 | Fuss et al. |
| 2002/0068975 A1 | 6/2002 | Teitelbaum |
| 2002/0082598 A1 | 6/2002 | Teitelbaum |
| 2002/0082600 A1 | 6/2002 | Shaolian et al. |
| 2002/0107519 A1 | 8/2002 | Dixon et al. |
| 2002/0116006 A1 * | 8/2002 | Cohen ............... 606/99 |
| 2002/0161368 A1 | 10/2002 | Foley et al. |
| 2002/0173796 A1 | 11/2002 | Cragg |
| 2002/0198526 A1 | 12/2002 | Shaolian |
| 2003/0004517 A1 | 1/2003 | Anderson |
| 2003/0060826 A1 | 3/2003 | Foley et al. |
| 2003/0073998 A1 | 4/2003 | Pagliuca et al. |
| 2003/0083688 A1 | 5/2003 | Simonson |
| 2003/0139648 A1 | 7/2003 | Foley et al. |
| 2003/0195518 A1 | 10/2003 | Cragg |
| 2003/0199871 A1 | 10/2003 | Foley et al. |
| 2003/0199872 A1 | 10/2003 | Markworth et al. |
| 2003/0199884 A1 | 10/2003 | Davison et al. |
| 2003/0204189 A1 | 10/2003 | Cragg |
| 2003/0208202 A1 | 11/2003 | Falahee |
| 2003/0225408 A1 | 12/2003 | Nichols et al. |
| 2003/0229353 A1 | 12/2003 | Cragg |
| 2004/0006341 A1 | 1/2004 | Shaolian |
| 2004/0006344 A1 | 1/2004 | Nguyen |
| 2004/0034351 A1 | 2/2004 | Sherman et al. |
| 2004/0039384 A1 | 2/2004 | Boehm, Jr. |
| 2004/0059333 A1 | 3/2004 | Carl et al. |
| 2004/0082954 A1 | 4/2004 | Teitelbaum |
| 2004/0082960 A1 | 4/2004 | Davison |
| 2004/0082961 A1 | 4/2004 | Teitelbaum |
| 2004/0087950 A1 | 5/2004 | Teitelbaum |

| | | | |
|---|---|---|---|
| 2004/0093001 A1 | 5/2004 | Hamada | |
| 2004/0106934 A1 | 6/2004 | Grossman | |
| 2004/0133201 A1 | 7/2004 | Shluzas et al. | |
| 2004/0138662 A1 | 7/2004 | Landry et al. | |
| 2004/0143265 A1 | 7/2004 | Landry et al. | |
| 2004/0143268 A1 | 7/2004 | Falahee | |
| 2004/0147928 A1 | 7/2004 | Landry et al. | |
| 2004/0147936 A1 | 7/2004 | Rosenberg et al. | |
| 2004/0172022 A1 | 9/2004 | Landry et al. | |
| 2004/0176763 A1 | 9/2004 | Foley | |
| 2004/0194791 A1 | 10/2004 | Sterman et al. | |
| 2004/0215190 A1 | 10/2004 | Nguyen | |
| 2004/0215193 A1 | 10/2004 | Shaolian et al. | |
| 2004/0236317 A1 | 11/2004 | Davison | |
| 2004/0254576 A1 | 12/2004 | Dunbar, Jr. et al. | |
| 2005/0010220 A1 | 1/2005 | Casutt et al. | |
| 2005/0010221 A1 | 1/2005 | Dalton | |
| 2005/0021030 A1 | 1/2005 | Pagliuca et al. | |
| 2005/0021031 A1 | 1/2005 | Foley et al. | |
| 2005/0033297 A1 | 2/2005 | Davison | |
| 2005/0038432 A1 | 2/2005 | Shaolian et al. | |
| 2005/0038434 A1 | 2/2005 | Mathews | |
| 2005/0043741 A1 | 2/2005 | Michelson | |
| 2005/0043742 A1 | 2/2005 | Bruneau et al. | |
| 2005/0059969 A1 | 3/2005 | McKinley | |
| 2005/0065515 A1 | 3/2005 | Jahng | |
| 2005/0065517 A1 | 3/2005 | Chin | |
| 2005/0070917 A1 | 3/2005 | Justis | |
| 2005/0080418 A1 | 4/2005 | Simonson et al. | |
| 2005/0085813 A1 | 4/2005 | Spitler et al. | |
| 2005/0090822 A1 | 4/2005 | DiPoto | |
| 2005/0090833 A1 | 4/2005 | DiPoto | |
| 2005/0113833 A1 | 5/2005 | Davison | |
| 2005/0124991 A1 | 6/2005 | Jahng | |
| 2005/0131407 A1 | 6/2005 | Sicvol et al. | |
| 2005/0131408 A1 | 6/2005 | Sicvol et al. | |
| 2005/0131421 A1 | 6/2005 | Anderson et al. | |
| 2005/0131422 A1 | 6/2005 | Anderson et al. | |
| 2005/0137461 A1 | 6/2005 | Marchek et al. | |
| 2005/0137593 A1 | 6/2005 | Gray et al. | |
| 2005/0149022 A1 | 7/2005 | Shaolian et al. | |
| 2005/0149035 A1 | 7/2005 | Pimenta et al. | |
| 2005/0154389 A1 | 7/2005 | Selover et al. | |
| 2005/0171540 A1 | 8/2005 | Lim et al. | |
| 2005/0192570 A1 | 9/2005 | Jackson | |
| 2005/0245928 A1 | 11/2005 | Colleran et al. | |
| 2005/0251139 A1 | 11/2005 | Roh | |
| 2005/0277942 A1 | 12/2005 | Kullas et al. | |
| 2006/0111713 A1 | 5/2006 | Jackson | |
| 2006/0111714 A1 | 5/2006 | Foley | |
| 2006/0200135 A1 | 9/2006 | Sherman et al. | |
| 2006/0247658 A1 | 11/2006 | Pond et al. | |
| 2008/0009864 A1 | 1/2008 | Forton et al. | |

FOREIGN PATENT DOCUMENTS

| | | |
|---|---|---|
| DE | 10027988 | 1/2002 |
| EP | 0 528 177 | 2/1993 |
| EP | 528562 A2 | 2/1993 |
| EP | 611116 A1 | 8/1994 |
| EP | 611116 B1 | 7/1996 |
| EP | 665731 A4 | 1/1997 |
| EP | 1006888 A4 | 6/2000 |
| EP | 1 027 988 | 8/2000 |
| EP | 1248568 B1 | 9/2003 |
| EP | 1 374 786 | 1/2004 |
| EP | 1468652 A1 | 10/2004 |
| EP | 1 545 355 | 6/2005 |
| SU | 839513 | 6/1981 |
| WO | WO9318722 A1 | 9/1993 |
| WO | WO9409726 A1 | 5/1994 |
| WO | WO-95/14437 | 6/1995 |
| WO | WO9714457 A1 | 4/1997 |
| WO | WO9836785 A1 | 8/1998 |
| WO | WO9838918 A1 | 9/1998 |
| WO | WO9929242 A1 | 6/1999 |
| WO | WO9951139 A2 | 10/1999 |
| WO | WO0045720 A1 | 8/2000 |
| WO | WO0112080 A1 | 2/2001 |
| WO | WO0137744 A2 | 5/2001 |
| WO | WO0141681 A1 | 6/2001 |
| WO | WO0156479 A1 | 8/2001 |
| WO | WO0160232 A3 | 8/2001 |
| WO | WO0160234 A2 | 8/2001 |
| WO | WO0160262 A1 | 8/2001 |
| WO | WO0160263 A1 | 8/2001 |
| WO | WO0160270 A1 | 8/2001 |
| WO | WO0195823 A1 | 12/2001 |
| WO | WO0160262 C2 | 10/2002 |
| WO | WO02085217 A2 | 10/2002 |
| WO | WO0160270 C2 | 11/2002 |
| WO | WO03020110 A2 | 3/2003 |
| WO | WO-03/028566 | 4/2003 |
| WO | WO03037170 A2 | 5/2003 |
| WO | WO03057055 A1 | 7/2003 |
| WO | WO03079914 A1 | 10/2003 |
| WO | WO03088810 A2 | 10/2003 |
| WO | WO03088878 A1 | 10/2003 |
| WO | WO2004004584 A1 | 1/2004 |
| WO | WO2004017847 A2 | 3/2004 |
| WO | WO2004021899 A1 | 3/2004 |
| WO | WO2004028382 A2 | 4/2004 |
| WO | WO-2004/041100 | 5/2004 |
| WO | WO2004037070 A2 | 5/2004 |
| WO | WO2004037074 A2 | 5/2004 |
| WO | WO2004058045 A2 | 7/2004 |
| WO | WO2004080318 A1 | 9/2004 |
| WO | WO2005018466 A2 | 3/2005 |
| WO | WO2005023123 A1 | 3/2005 |
| WO | WO-2005/032358 | 4/2005 |
| WO | WO-2005/060534 A | 7/2005 |
| WO | WO-2005/072081 | 8/2005 |
| WO | WO-2006/116662 | 11/2006 |

OTHER PUBLICATIONS

Synthes; *MIRA For M.I.S.S*, Surgical Technique Brochure. Synthes, p. 1-7.
Encore Spine; *Degenerative System*, Encore Surgical Product Brochure, p. 1-6.
Bare Bones; *Monthly Executive Summary*, vol. 12 No. 1 Jan. 2003 p. 1-4.
Sofamor Danek; *Sextant CD Horizon Sextant Rod Insertion System*. Surgical Techniques pg. 1-29.
Sofamor Danek; *Sextant CD Horizon Sextant Rod Insertion System*, Sofamor Danek Web page.
Sofamor Danek; *Eclipse CD Horizon Eclipse Implants and Instruments*, Information from the Sofamor Danek Web page, p. 1-3.
Sofamor Danek; *Metrx, X-Tube, Retraction System*; Sofamor Danek Web page information, p. 1-2.
Smith and Nephew; *6.5mm and 4.0 mm Cannulated Screws*, Surgical Technique p. 1-24.
Nuvasive; *SpheRx DBR Minimally Disruptive Fixation*, Nuvasive web page information. 1 page.
Spinal Concepts; *Access Dilation Port*, Spinal Concepts Web Page information 2 pages.
Charles Hartjen; *The Atavi System*, Surgical Technique Brochure. Endius, p. 1717.
Maxcess; *Decompression Surgical Technique*. Nuvasive Creative Spine Technology Product Brochure, p. 1-16.
Pathfinder; *Minimally invasive Spinal Fixation System and Surgical Technique*. Spinal Concepts Product Brochure, p. 1-26.
Pathfinder; *Minimally Invasive Pedicle Fixation System*. Spinal Concepts Product Brochure p. 1-4.
Leu et al., Percutaneous Fusion of the Lumbar Spine, State of the Art Reviews, vol. 6, No. 3, pp. 593-604, 9-92.
Kambin, Arthroscopic Lumbar Intervertebral Fusion, Chapter 95, The Adult Spine, vol. 2, pp. 2037-2046, 1997.
Kambin et al., Anterior Column Support for Failed Fusion, Revision Spine Surgery, pp. 589-600, date not known.
Kambin, The Role of Minimally Invasive Surgery in Spinal Disorders, Advance Operative Orthopedics, vol. 3, pp. 147-171, 1995.
Kambin, "Arthroscopic Microdiscectomy", The Journal of Arthroscopy, vol. 8, No. 3, 1992, pp. 287-295.
Kambin et al, "Percutaneous Posterolateral Lumbar Discectomy and Decompression with a 6.9-millimeter cannula", The Journal of Bone and Joint Surgery, Jul. 1991, pp. 822-831.

Kambin, "Arthroscopic Microdiskectomy", The Mount Sinai Journal of Medicine, vol. 58, No. 2, Mar. 1991, pp. 159-164.

Kambin, "Posterolateral Percutaneous suction-excision of herniated lumbar intervertebral disc", Clinical Orthopaedics and Related Research. No. 207, Jun. 1988, pp. 37-42.

Kambin, Posterolateral Percutaneous Lumbar Interbody Fusion, Arthroscopic Microdiscectomy, pp. 117-121, 1991.

Kambin, Posterolateral Percutaneous Lumbar Discectomy and Decompression Arthroscopic Microdiscectomy, Section IV. pp. 67-100, 1991.

Kambin, Minimally Invasive Techniques in Spinal Surgery Current Practice, Neurosurgical.

Diapason, Surgical Texchnique Catalog, Diapasan Spinal System, Jan. 2002.

Maxcess; XLIF 90° Surgical Technique. Nuvasive Creative Spine Technology Product Brochure, p. 1-26.

Office Action from U.S. Appl. No. 11/526,785, dated Jan. 8, 2009.

Office Action from U.S. Appl. No. 11/202,487, dated Dec. 9, 2008.

U.S. Appl. No. 11/526,785, filed Sep. 25, 2006.

U.S. Appl. No. 12/316,637, filed Dec. 15, 2008.

U.S. Appl. No. 11/202,487, filed Aug. 12, 2005.

* cited by examiner

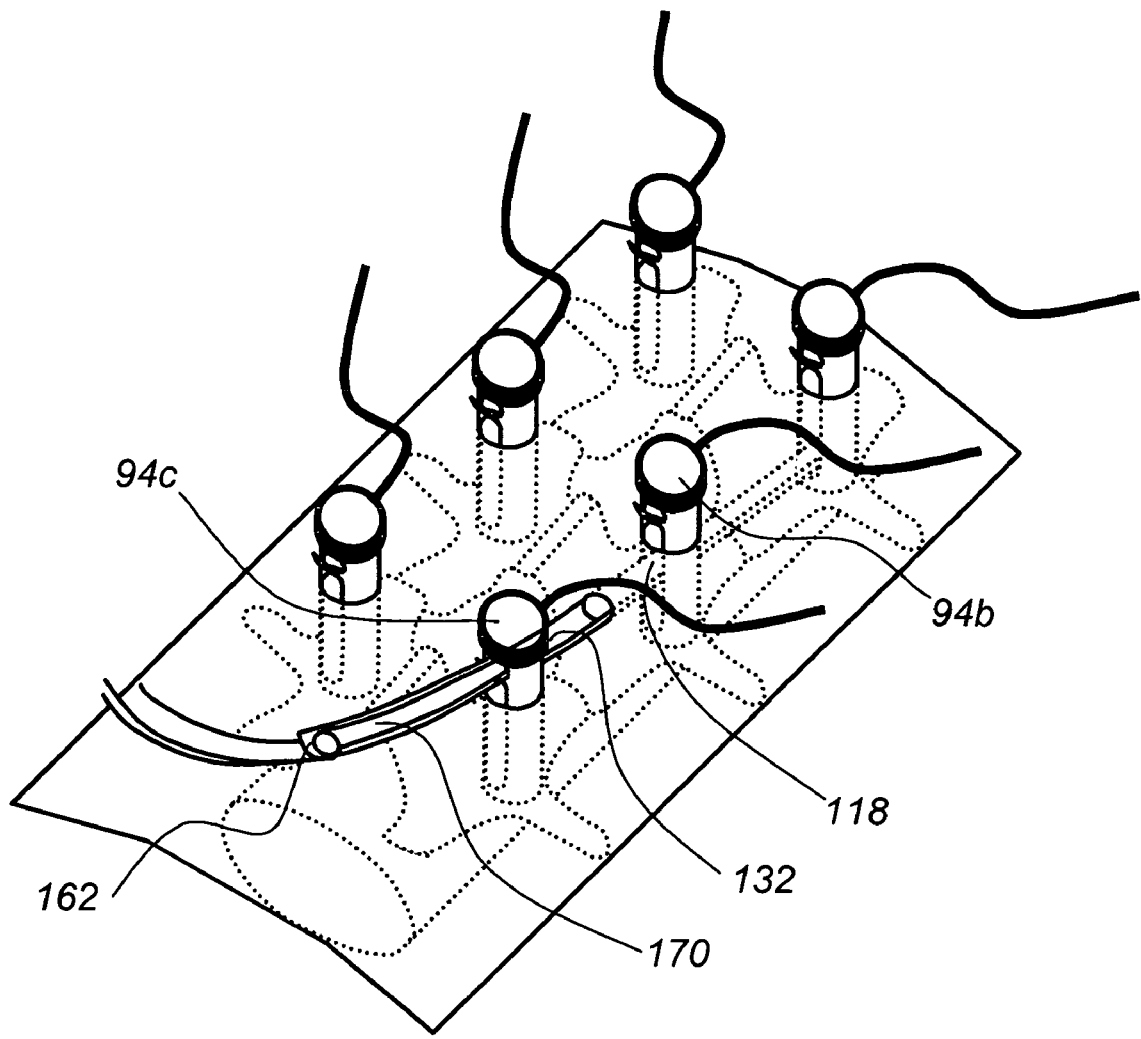
FIG. 9
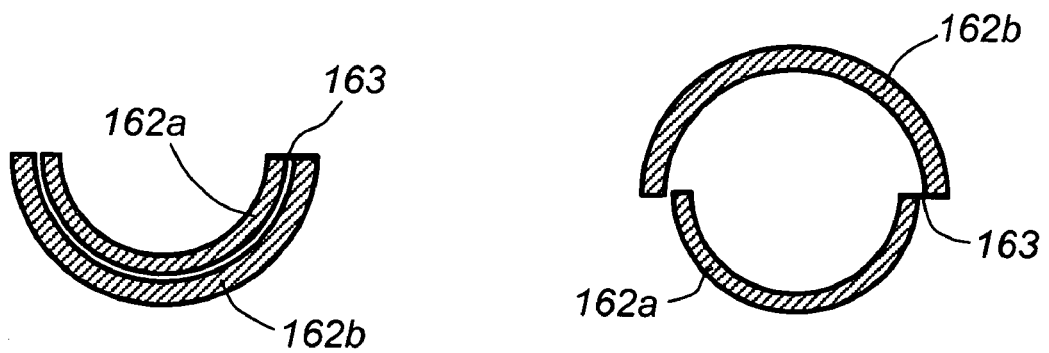
FIG. 9A
FIG. 9B

METHODS AND DEVICES FOR IMPROVING PERCUTANEOUS ACCESS IN MINIMALLY INVASIVE SURGERIES

CROSS REFERENCE TO RELATED CO-PENDING APPLICATIONS

This application is a continuation in part of U.S. application Ser. No. 10/669,927 filed on Sep. 24, 2003 now U.S. Pat. No. 7,282,064 and entitled APPARATUS AND METHOD FOR CONNECTING SPINAL VERTEBRAE the contents of which are expressly incorporated herein by reference. This application also claims the benefit of U.S. provisional application Ser. No. 60/518,580 filed on Nov. 8, 2003 and entitled METHODS AND DEVICES FOR IMPROVING PERCUTANEOUS ACCESS the contents of which are expressly incorporated herein by reference.

FIELD OF THE INVENTION

The present invention relates to methods and devices for improving percutaneous access in minimally invasive surgeries, and more particularly to methods and devices that provide variable length access channels to locations deep within a patient's body, and allow the percutaneous transfer of connecting devices and instruments within one access channel or between two or more adjacent access channels placed deep in two or more locations of the patient's body, respectively.

BACKGROUND OF THE INVENTION

It is well known that traditional surgical procedures in locations deep within a patient's body require a long incision, extensive muscle stripping, prolonged retraction of muscles for visualization, and denervation and devascularization of the adjacent tissue. These procedures result in extensive tissue traumatization and consequently in prolonged recovery time, risk of infections, high hospitalization costs, pain that can be more severe than the pain due to the initial ailment, and in some cases permanent scarring. In minimally invasive surgical procedures, portals are used to access the locations deep in the patient's body. The use of portals rather than a long incision causes less trauma to the adjacent tissue, reduces the recovery time and pain and may be performed in some case under only local anesthesia. The avoidance of general anesthesia reduces post-operative recovery time and the risk of complications.

Minimally invasive surgical procedures are especially desirable for spine surgeries because spine pathologies are located deep within the body without clear muscle planes and there is danger of damaging the adjacent neural and vascular tissues. In treating the majority of spinal pathologies, the spinal muscles are stripped from the bony elements of the spine followed by laminectomy to expose the dura, the nerve roots, and the discs. The incision has to be wide enough and the tissues have to be retracted to maintain a channel from the skin to the floor of the spinal canal that will allow direct visualization. This is similar to an open surgery approach to the knee to expose the menisci versus minimally invasive alternatives such as an arthroscopy which uses 1 centimeter portals under illuminated magnification which results in improved visualization, reduced postoperative knee pain, recovery time, and the destruction of healthy tissue. The destruction to the spinal structures is even more extensive during fusion procedures, which require more lateral tissue dissection and exposure to access the transverse processes and pedicles for placement of pedicle screws, rod constructs for stability, and bone graft under direct vision.

Multiple attempts have been made to improve the techniques, devices, and instrumentations used for minimal and percutaneous surgery. These include use of percutaneous needle administration of chemonucleolytic agents to enzymatically dissolve the disc and the use of microscopes and loupe magnification to limit the incision size. These two approaches are at the foundation of minimal access surgery, one using an injectable agent and the other using a device to limit the exposure while maximizing the visualization. Unfortunately, the effectiveness and safety of the enzyme, chymopapain used for chemonucleolysis, have been complicated by severe spasms, post-operative pain, and sensitivity reactions including anaphylactic shock. Loupe magnification and microscopes are helpful for improving visualization but are not effective without retractor systems and specialized instruments and devices to make minimal access surgery effective.

Substantial progress has been made to develop the necessary devices, instruments, and methods to effectively improve minimal access surgery resulting in improved visualization, less tissue injury, less general anesthesia exposure and improved recovery time and post-operative pain. For example U.S. Pat. Nos. 5,792,044 and 5,902,231 by Foley et al., demonstrate some of the improved methods and instruments for percutaneous surgeries.

A problem that occurs frequently in minimally invasive surgical procedures is related to the fact that it is not always known how deep the pathology is located. Accordingly there is a need for a portal with a variable length to accommodate the locations of the various pathologies.

Furthermore, in spine fusion procedures connecting elements, such as rods, plates or wires are placed and fixed between two or more locations of the spine. Placement of these connecting elements requires open surgery, which is currently one of the major limitations of other percutaneous cannula access methodologies. Accordingly there is a need for inserting and placing these connecting elements between two or more separate spinal locations without performing open surgery.

SUMMARY OF THE INVENTION

In general, in one aspect, the invention features a device for use as a portal in percutaneous minimally invasive surgery performed within a patient's body cavity. The device includes a first elongated hollow tube having a proximal end and a distal end and defining a first working channel between the proximal end and the distal end when placed within the body cavity. The first tube has a mechanism for adjusting the length of the first tube within the patient's body cavity.

Implementations of this aspect of the invention may include one or more of the following features. The first tube includes an inner hollow tube and an outer hollow tube and the inner hollow tube is adapted to slide within the outer hollow tube thereby providing the mechanism for adjusting the first tube length. The inner hollow tube comprises an outer surface having an elongated groove extending along a length segment of the outer surface, the outer hollow tube comprises an inner surface having an elongated appendage extending along a length segment of the inner surface, and the appendage is adapted to slide within the groove thereby providing the mechanism for adjusting the first tube length. The inner hollow tube comprises an outer surface having an elongated appendage extending along a length segment of the outer surface, the outer hollow tube comprises an inner surface having an elongated groove extending along a length segment of the inner surface, and the appendage is adapted to slide within the groove thereby providing the mechanism for adjusting the first tube length. The inner hollow tube comprises a first slot opening extending the entire width of the inner hollow tube, the outer tube comprises a second slot opening extending the entire width of the outer hollow tube and the first slot opening is aligned with the second slot opening when the inner hollow tube is assembled within the outer hollow tube, thereby forming a continuous opening extending the entire width of the first tube. The first tube further comprises a second hollow tube extending from a side opening of the first tube located outside the body cavity and forming a second working channel and wherein the second working channel is in communication with the first working channel through an opening in the wall of the outer hollow tube. The first and second tubes are sized for delivering carrier devices, surgical instruments, medical devices, fixation devices, vertebral disc replacement devices, interbody devices, fixation tools, connecting devices, connecting tools, tissue, grafting material, or illumination devices, to a pathology location within the body cavity. The surgical instruments may be scissors, scalpels, saws, drills, tissue dilators, biting and grabbing instruments, curettes, knot tying, or cautery. The fixation devices may be screws, hooks, loops, pins, nuts, washers, wires, sutures, or staples. The fixation tools may be screw drivers, pushers, holders, wrenches, staplers, or knot tiers. The connecting devices may be plates, rods, wires, vertebral disc replacements, interbody fusion devices, or articulating versions thereof. The connecting tools may be connecting tools carriers, pushers, screw drivers, and wrenches. The illumination devices may be light sources, fiber optic cables, infrared detectors, magnification devices, and microscopes. The first tube may further comprise a mechanism for engaging and disengaging a fixation device. The first tube may comprise a slot at the distal end and the slot is sized to engage an appendage of the fixation device and secure the fixation device through a clock-wise rotation around a longitudinal axis of the first working channel, thereby providing the engaging mechanism for engaging the fixation device. The device may further comprise disengaging the fixation device by performing a counter-clock-wise rotation around the longitudinal axis. Alternatively, the first tube may engage or disengage the appendage of the fixation device via an anti-clockwise rotation or a clockwise rotation, respectively. The continuous opening may be sized for delivering surgical equipment, medical devices, intervertebral disc replacement devices, interbody fusion devices, fixation devices, fixation tools, carrier devices, connecting devices, connecting tools, tissue, grafting material, or illumination devices, from the first working channel of the first elongated tube to a first working channel of second elongated tube located adjacent to the first elongated tube. The carrier devices may comprise flexible, malleable, rigid, or materials that are expandable at body temperature. The inner or the outer hollow tubes may comprise a taper along their length. The first tube may further comprise a manually adjustable mechanism for adjusting the first tube length within or outside the body cavity. The outer cannula may have millimeter markers etched on the outside to allow the user to determine the depth of the pathology with respect to the skin surface. The first tube may comprise an inner hollow tube having an outer cylindrical surface with a first set of helical threads and an outer hollow tube having an inner cylindrical surface with a second set of helical threads. In this case, the outer hollow tube is adapted to rotate around the inner hollow tube while engaging the second set of helical threads with the first set of helical threads, thereby causing the inner hollow tube to move longitudinally relative to the outer hollow tube and thereby providing the mechanism for adjusting the length of the first tube. The inner hollow tube may be adapted to slide within a space formed between an inner cylindrical wall and an inner planar wall of the outer hollow tube. The inner hollow tube may be adapted to slide within a space formed between an inner cylindrical wall of the outer tube and an outer cylindrical wall of a second hollow tube placed concentric with the inner and outer hollow tubes.

In general, in another aspect the invention features a system for use in minimally invasive percutaneous surgery including two or more elongated hollow tubes placed within two or more adjacent body cavities of a patient, respectively. Each of the two or more hollow tubes comprises a proximal end and a distal end defining a first working channel between the proximal end and the distal end and at least one of the two or more hollow tubes comprises a mechanism for adjusting its length.

Implementations of this aspect of the invention may include one or more of the following features. The two or more hollow tubes define two or more first working channels, respectively, and the two or more hollow tubes comprise two or more side openings extending the entire width of the two or more tubes, respectively, and the two or more side openings are aligned with each other and are sized for allowing transferring of objects between the two or more first working channels. The objects may be surgical equipment, medical devices, intervertebral disc replacement devices, interbody fusion devices, fixation devices, fixation tools, carrier devices, connecting devices, connecting tools, tissue, grafting material, or illumination devices. The two or more side openings are located in areas of the two or more tubes, respectively, positioned within the two or more adjacent body cavities, respectively. The system may also include a carrier device for transferring devices between the two or more elongated hollow tubes through the aligned side openings. This carrier device may be made of a material that is stiff, malleable, flexible or expandable at body temperature. The system may further include direct or indirect visualization of the two or more first working channels.

In general, in another aspect the invention features a method for performing percutaneous minimally invasive surgery on a patient including inserting a first elongated hollow tube within a first body cavity of the patient, wherein the first tube has a proximal end and a distal end and defining a first working channel between the proximal end and the distal end when placed within the first body cavity and wherein the first tube comprises a mechanism for adjusting the first tube length within the first body cavity.

Implementations of this aspect of the invention may include one or more of the following features. The method may further include before inserting the first tube into the first body cavity making a first incision on a first location of the patient's skin, then advancing a first guide wire through the first incision, through tissue underlying the first location and into a first underlying bone and forming the first body cavity around the first guide wire. The first body cavity is formed by advancing a tissue dilator over the first guide wire. The method may further include placing a fixation device over the guide wire and engaging the distal end of the first tube to a fixation device in the first body cavity. Alternatively, the method may further include engaging a fixation device to the distal end of the first tube before inserting the first tube into the first body cavity, then attaching the fixation device to a first bone within the first body cavity after inserting the first tube into the first body cavity and disengaging the fixation device from the distal end of the first tube. The method may also include adjusting the first tube length via a self-contained adjusting mechanism. The first tube comprises an inner hollow tube and an outer hollow tube and wherein the inner hollow tube is adapted to slide within the outer hollow tube thereby providing the self-contained mechanism for adjusting the first tube length. The method may also include inserting a cutting tool into the first tube and incising tissue around the first body cavity. The first tube comprises a first opening extending the entire width of the first tube and being located in a portion of the first tube within the first body cavity and wherein the cutting tool is used to incise tissue around the first body cavity through the first opening. The method may also include inserting a second elongated hollow tube within a second body cavity of the patient adjacent to the first body cavity, wherein the second tube has a proximal end and a distal end and defining a second working channel between the proximal end and the distal end when placed within the second body cavity and wherein the second tube comprises an adjustable length. The method also includes incising tissue between the first body cavity and the second body cavity, thereby forming a path extending from the first body cavity to the second body cavity, then inserting a connecting device into the first tube and then transferring the connecting device from the first tube to the second tube through the path. The method also includes attaching a first end of the connecting device to a first bone within the first body cavity via a first fixation device and attaching a second end of the connecting device to a second bone within the second body cavity via a second fixation device. The first bone within the first body cavity may be a first vertebra, and the second bone within the second body cavity may be a second vertebra. The first and second fixation devices may be screws, hooks, loops, pins, nuts, washers, wires, sutures, or staples. The connecting device may be plates, rods, wires or articulating versions thereof. The connecting devices may be transferred within a carrier device and the carrier device may have a boat-shaped body with a closed front end. The tissue between the first and the second body cavities may be a lumbodorsal fascia and the path is located either above or below the lumbodorsal fascia. The first and second tubes are sized for delivering carrier devices, surgical instruments, fixation devices, fixation tools, connecting devices, connecting tools, tissue, grafting material, or illumination devices, to a pathology location within the body cavity. The method may also include inserting additional elongated tubes within additional body cavities of the patient adjacent to the first and second body cavities. The method may also include making a second incision on a second location of the patient's skin, then advancing a second guide wire through the second incision, through tissue underlying the second location and into a second underlying bone, then forming the second body cavity around the second guide wire and finally removing the first and second tubes from the first and second body cavities and closing the first and the second incisions.

Among the advantages of this invention may be one or more of the following. The invention provides novel devices and methods for improving percutaneous surgeries for all applications and approaches in the body that previously required open surgery. These improvements will be beneficial to both patients and surgeons in that this invention will reduce the technical difficulty of these operations, improve visualization, decrease risks of iatrogenic injuries to vital structures, decrease length of hospitalization and associated costs, decrease operative time, decrease recovery time, and decrease postoperative pain. This invention provides the ability to adjust the length of the minimal access portals either inside or outside the patient to account for the varying depth of the pathology within the body. The graduated markers in millimeter increments etched on the outside of the cannula allow a determination of the depth of the pathology relative to the skin thus allowing the user to make adjustments to the fixation points such that they are aligned to the same depth. The invention further allows fixing two points percutaneously along the lateral aspect of the spine by directly placing the connecting device between the fixation points without visualizing the entire connecting device or by coming in along an arc or using fluoroscopic imaging. The invention also provides the ability to sequentially connect a fixation device percutaneously between more than two points simultaneously and only directly visualizing the fixation points and not the entire connecting device. This scaleable feature is currently a major limitation of other minimal access devices. Another advantage of this invention is the ability to perform a direct approach to the fixation of two or more points with the option to place the connecting device beneath the lumbodorsal fascia or through an incision, created by instruments in the lumbodorsal fascia between each fixation points rather than being confined to go beneath the fascia between the fixation points or through a larger opening in the fascia which requires greater tissue expansion and results in greater postoperative pain. The invention also provides a device that easily connects the portals at the sequential fixation points and simultaneously delivers objects such as connecting devices, or tools between the fixation points even if the fixation points are not in a perfectly straight line. The invention also provides the ability to lock the working cannula to the pedicle screw and is the first pedicle screw to feature an appendage for connecting a percutaneous device. It is the first device to allow easy retrieval of a medical device in contrast to the other systems that are designed for insertion of medical devices without a method or features that are designed for retrieval of the device. The cannulae can be easily removed from the fixation points and have the ability to reconnect to the fixation points and remove the connecting device even after having completed the surgery or after connecting the device to the fixation points and removing the cannulae. The invention also provides a side-working channel in addition to the central working channel to allow easier placement of connecting devices between fixation points without obstructing the visual portal as in other devices with only a single working channel that also doubles as a visualization channel. The invention also provides a fixed or rotating apparatus at various positions on any of the working channels or portals that can be used for optics, illumination, irrigation, or aspiration or combination thereof. The invention also provides a carrier device for carrying devices to be connected at the fixation points of the cannulae. This carrier device may be made of a material that is stiff, malleable, flexible or expandable at body temperature. By being malleable this carrier device may be used as a template on the skin surface between the cannulae prior to insertion and will be particularly beneficial when the cannulae do not line up in a straight line. The present invention has applications in a wide range of surgical procedures, and in particular in spinal procedures such as laminotomy, laminectomy, foramenotomy, facetectomy and discectomy, fusions or disc replacements using an anterior, posterior, postero-lateral, or a lateral approach to the disc space, facet, laminas, pedicles, or transverse processes. The devices and instruments of the present invention have application to surgical techniques that permit each of these several types of surgical procedures to be performed via a single or multiple sequential working channels. The present invention also has application to surgical techniques for preparing a disc space for insertion of an implant into the disc space.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views:

FIG. 9 is a top view of the patient's back as in FIG. 6 with a carrier device placed through a portal of this invention, the carrier device carrying a connecting rod for placement between adjacent vertebrae;

FIG. 9A is a cross-section of the front portion of a carrier device in the open position;

FIG. 9B is a cross-section of the front portion of the carrier device of FIG. 9A in the closed position;

DETAILED DESCRIPTION OF THE INVENTION

Figure 1A:
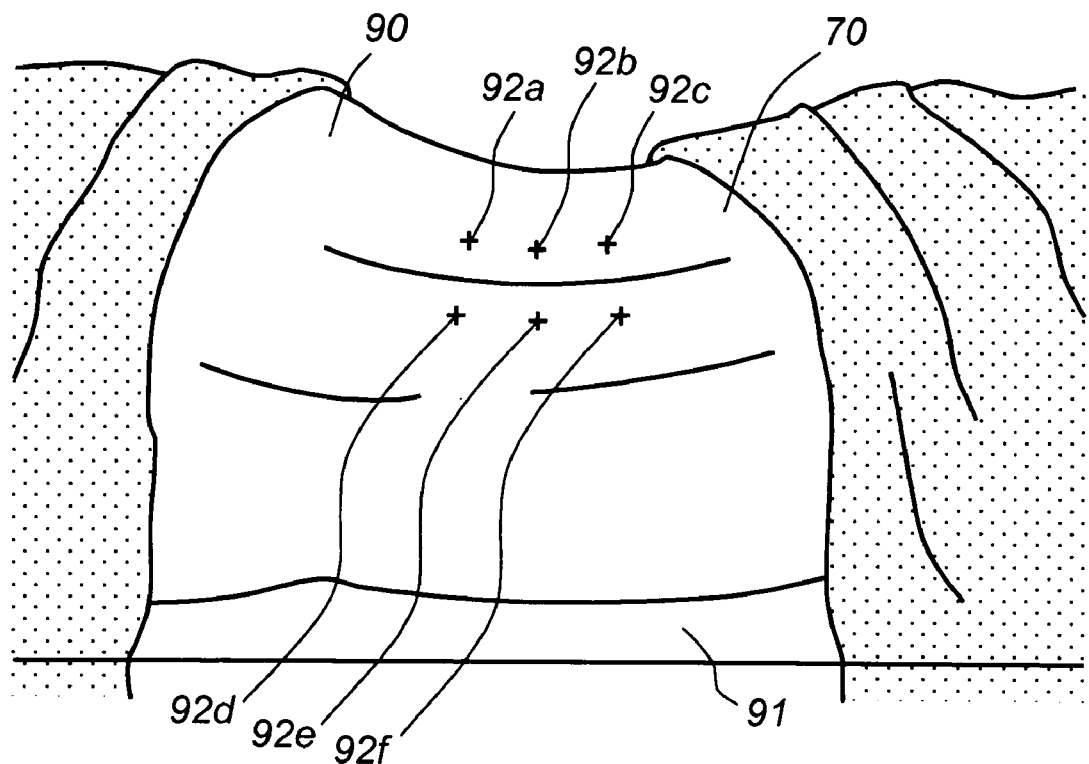
FIG. 1A is a top view of the back of a patient positioned prone on the operating table in preparation for spinal surgery.
Figure 1B:
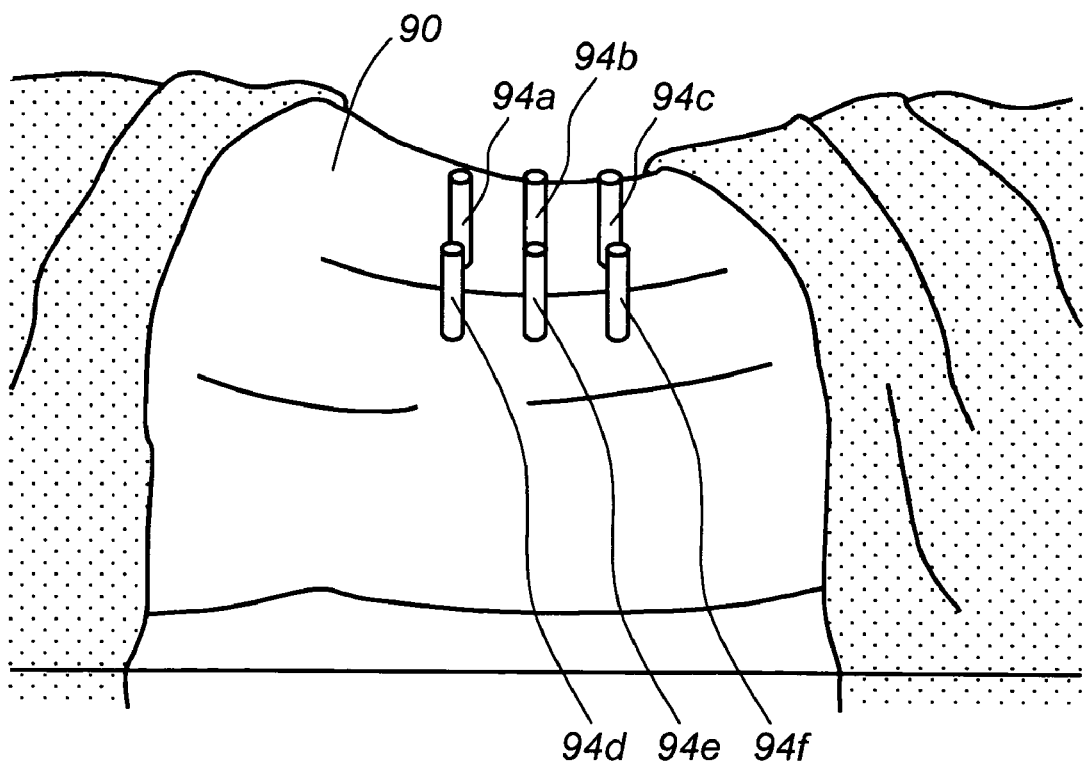
FIG. 1B is a top view of the patient's back with portals inserted in the areas of the pathology.

Referring to FIG. 1A, a patient 90 is positioned prone, lying flat on an operating table 91 in preparation for a minimally invasive surgery (MIS). Locations 92a-92f are marked on the patient's lower back corresponding to pedicle locations of adjacent vertebrae. For MIS procedures portals 94a-94f are inserted through skin incisions performed in the marked locations 92a-92f, respectively, shown in FIG. 1B.

Figure 2A:
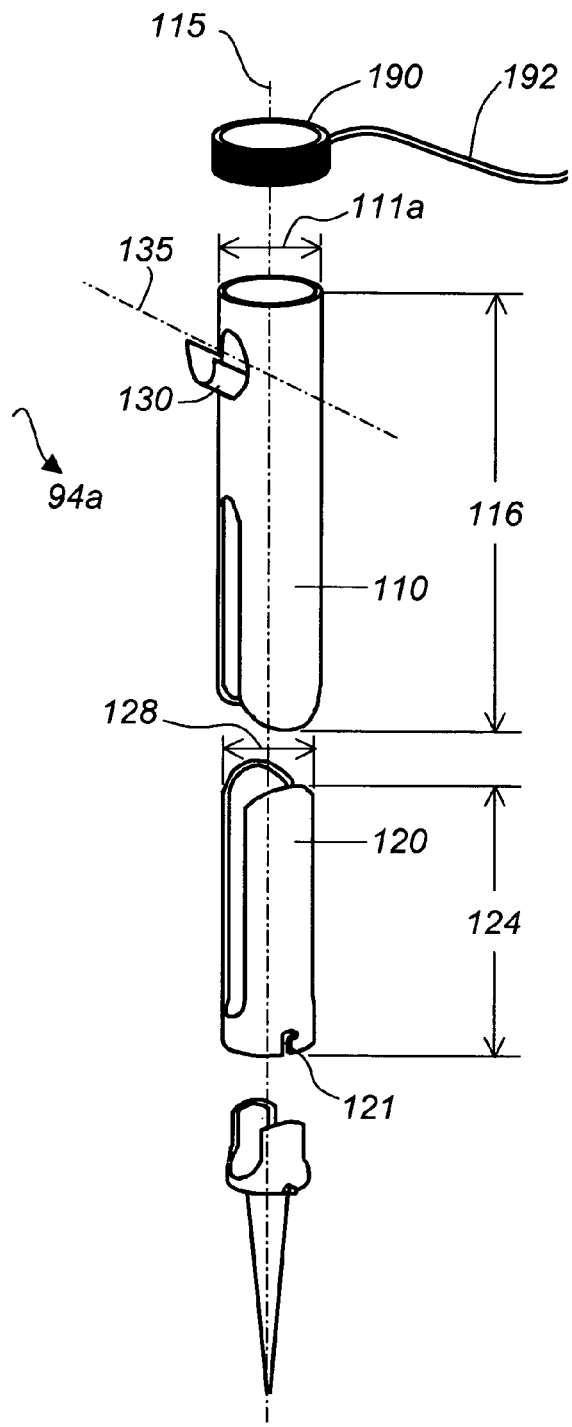
FIG. 2A is a perspective view of a portal with an adjustable length, according to this invention.
Figure 2B:
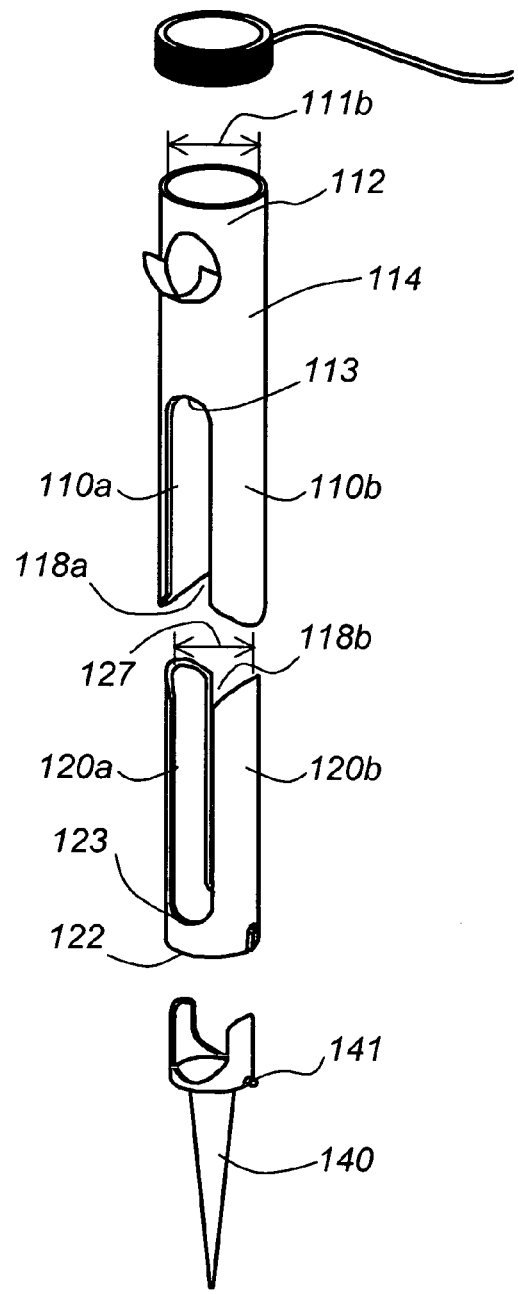
FIG. 2B is another perspective view of the portal of FIG. 2A.

According to one embodiment of this invention, shown in FIG. 2A, and FIG. 2B, portal 94a includes an outer elongated cannula 110 and an inner elongated cannula 120. Inner cannula 120 slides within outer cannula 110 and is secured at different locations of the inner wall of the outer cannula 110, thereby forming a first working channel 115 with adjustable length. This is especially desirable for reaching locations within the patient's body corresponding to the outer locations 92a-92f, that are at different distances from the patient's skin 70. Outer cannula 110 has millimeter markers 192 etched on the outside surface to allow determination of the depth of the pathology (shown in FIG. 17A). Portal 94a has an outer diameter sized for percutaneous placement within the patient's body. In one example, the outer diameter of portal 94a, as defined by the outer diameter 111a of the outer cannula 110, is 20 mm. Outer cannula 110 includes two elongated pieces 110a, 110b, extending from the distal end 113 of the main hollow cylindrical body 114 and forming an opening 118a between them. The proximal end 112 of the hollow cylindrical body 114 has a circular opening with an inner diameter 111b, and the previously mentioned outer diameter 111a. In one example, the outer cannula 110 has a length 116 of 40 mm, an inner diameter 111b of 18 mm and an outer diameter 111a of 20 mm. The outer cannula further includes a side portal 130 and an opening 132 located opposite to the side portal thereby defining a second working channel 135 (shown in FIG. 3C). The second working channel 135 communicates with the first working channel 115. In other embodiments, more than one side portals are included and may be located at any location along the outer or inner cannula or may be detachable. In another embodiment elongated pieces 10a and 110b may extend directly from the base of side portal 130. In another embodiment side portal 130 may communicate directly with the proximal opening of cylindrical body 114. In the embodiment of FIG. 2A, side portal 130 is fixed at an angle relative to the outer cannula 110. In other embodiments, side portal 130 may be hinged so that it can be placed at variable angles along the outer cannula 110. Side portal 130 functions as an automatic stop against the patient's skin 70, while the inner cannula 120 slides within the outer cannula 110 and elongates in order to reach the location of the pathology within the patient's body. Accordingly, the exposed length of the various outer cannulae above the skin may remain the same while the entire length of the portals variably elongates. It is important for the surgeon to have a consistent height of the cannula above the skin surface which may otherwise vary with different patient body habitus.

The inner cannula 120 includes a main hollow cylindrical body 122 and two elongated pieces 120a, 120b extending from the proximal end 123 of the main body 122. An opening 118b is formed between the two elongated pieces 120a, 120b. In one embodiment, inner cannula 120 further includes a slot 121 at the distal end of the main body 122 that functions as a docking element for attaching a device or a connecting element to the distal end of the inner cannula 120. In the example of FIG. 2A, the element shown 140 is a pedicle screw with an extension 141 that fits within the slot 121.

In one example, inner cannula 120 has a length 124 of 40 mm, an inner diameter 127 of 17 mm, and an outer diameter 128 of 17.75 mm. In other embodiments the outer diameter 128 may be in the range of 17.5 to 18 mm. In the embodiment of FIG. 2A, inner cannula 120 and outer cannula 110 have uniform inner and outer diameters. In other embodiments, the diameters may be non-uniform and the cannulae may be tapered at one or both ends. In other embodiments the opening 118b in cannula 120 may extend through the distal ends of both sides of cannula 120 without connecting the elongated pieces 120a and 120b or only on one side connecting either 120a or 120b.

Figure 2C:
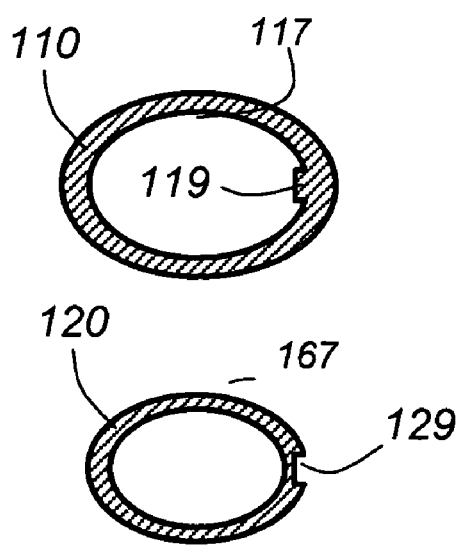
FIG. 2C is a cross-sectional view of the outer and inner cannulae of FIG. 2A.
Figure 2D:
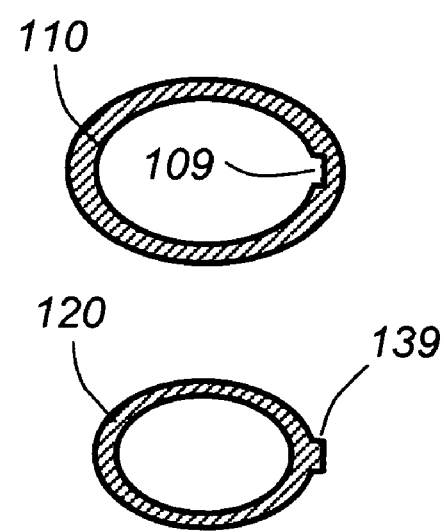
FIG. 2D is a cross-sectional view of another embodiment of the outer and inner cannulae of FIG. 2A.

Referring to FIG. 2C, the outer cannula 110 further includes an appendage 119 formed within the inner wall 117 of the outer cannula 110 and extending the entire length 116 of the cannula 110. Appendage 119 slides within a groove 129 formed on the outer wall 167 of cannula 120. Groove 129 extends the length 124 of the inner cannula 120 ending prior to reaching the top of cannula 120 so that there is a stop to complete separation of the cannulae as they elongate against each other and allows removal of the cannulae as one piece. Cannula 120 may have a lip at the top edge which overhangs to fit within the space within the wall of cannula 110 and stops against a ledge at the bottom of cannula 110. Alternatively, the outer cannula 110 may have a groove 109 in the inner wall 117 and the inner cannula 120 may have an appendage 139 in the outer wall 167 and the appendage 139 of the inner cannula 120 may slide within the groove 109 of the outer cannula 110 in a tongue and groove type fashion, as shown in FIG. 2D. Groove 109 ends prior to reaching the most distal surface of the outer cannula 110 so that there is a stop to complete separation of the cannulae as they elongate against each other and allows removal of the cannulae as one piece. In one embodiment the inner groves 109 and 129 may have serrations that allow a ratchet-type incremental elongation and shortening of the combined lengths of the cannulae 110 and 120. The ratchet-type mechanism also functions as a height securing mechanism which is an adjunct to the automatic height adjustment that occurs between the side portal 130 contacting the skin and the pedicle screw 140 contacting the vertebra as the cannulae elongate against each other. In other embodiments, the surfaces of the inner wall 117 and outer wall 167 are smooth.

Figure 17A:
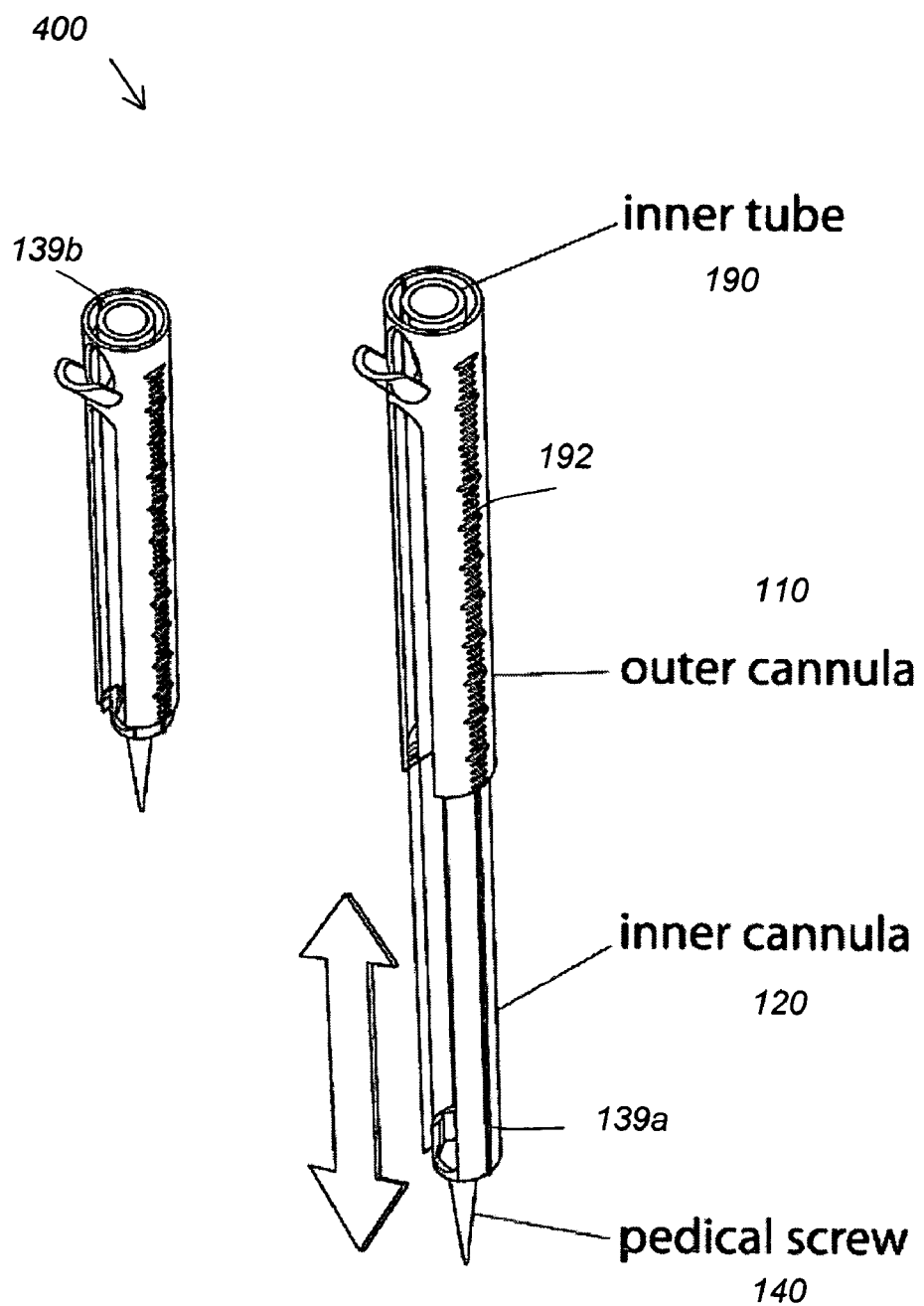
FIG. 17A is a perspective view of another embodiment of a portal with an adjustable length, according to this invention.
Figure 17B:
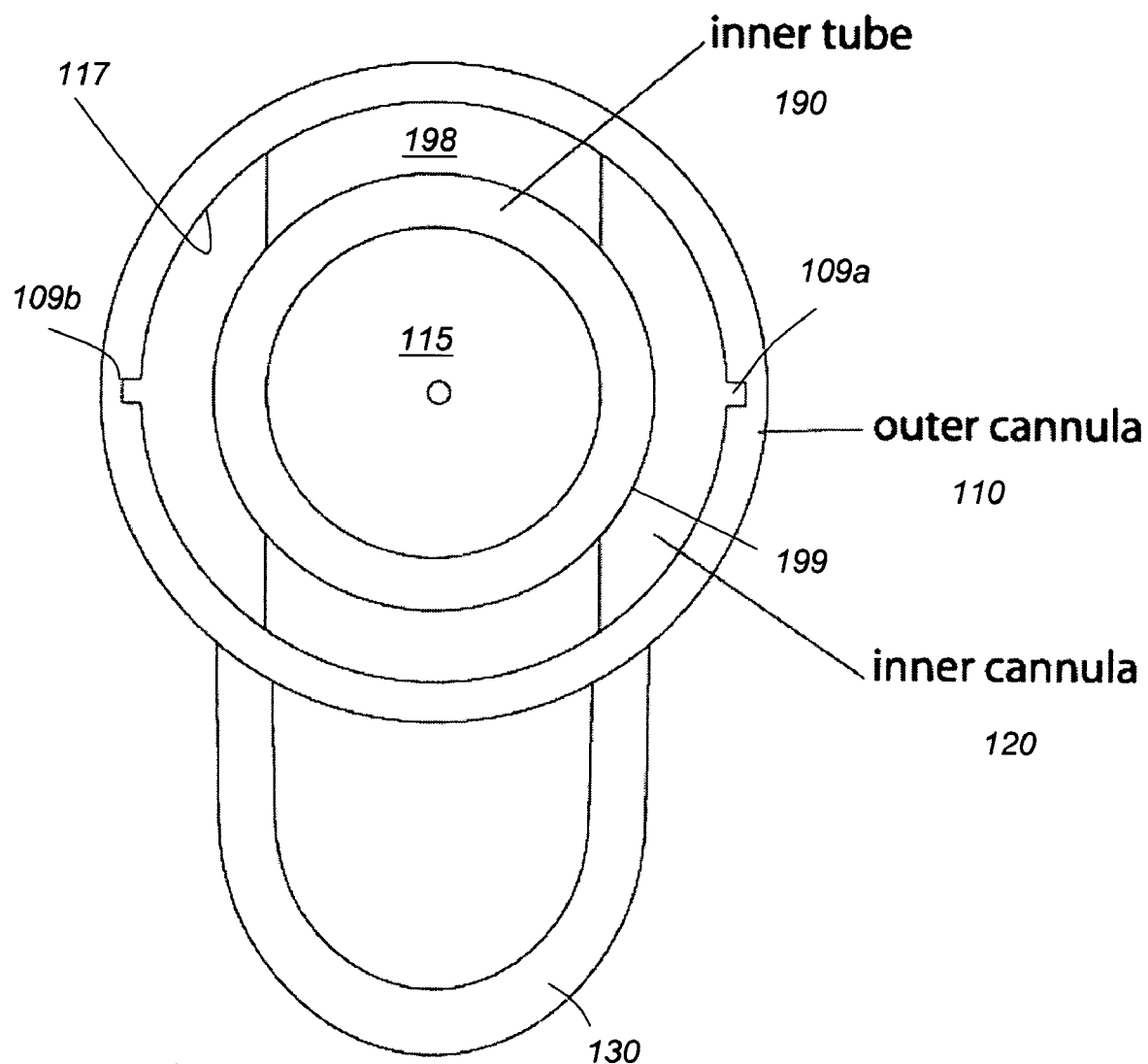
FIG. 17B is a top view of the embodiment of FIG. 17A.

The portal 94a dynamically adjusts its height automatically as the pedicle screw 140 advances within the pedicle since the distal end 122 of the inner cannula 120 is fixed to the screw 140 and each cannula 110, 120 is permitted to slide relative to each other. In another embodiment the inner cannula 120 slides within a space formed between the inner and outer diameter of cannula 110. Referring to FIGS. 17A and 17B, portal 400 includes an outer hollow cannula 110 and an inner hollow tube 190 placed with the hollow outer cannula 110. The diameter of the inner tube 190 is smaller than the inner diameter of the outer cannula 110 and a space 198 is formed between them. Inner cannula 120 is sized to fit within the space 198 and to slide against the inner wall 117 of the outer cannula 110 and the outer wall 199 of the inner tube 198. The inner wall 117 of outer cannula 110 includes a groove 109a extending the entire length 116 of the cannula 110 and the outer wall of the inner cannula 120 includes an appendage 139a. Appendage 139a slides within the groove 109a in a tongue and groove type configuration. Appendage 139a extends the length 124 of the inner cannula 120 ending prior to reaching the top of cannula 120 so that there is a stop to complete separation of the cannulae as they elongate against each other and allows removal of the cannulae as one piece. A second appendage 139b placed diametrically opposite the first appendage 139a on the outer wall of the inner cannula 120 slides within a second groove 109b placed diametrically opposite the first groove 109b on the inner wall of the outer cannula 110.

Figure 18A:
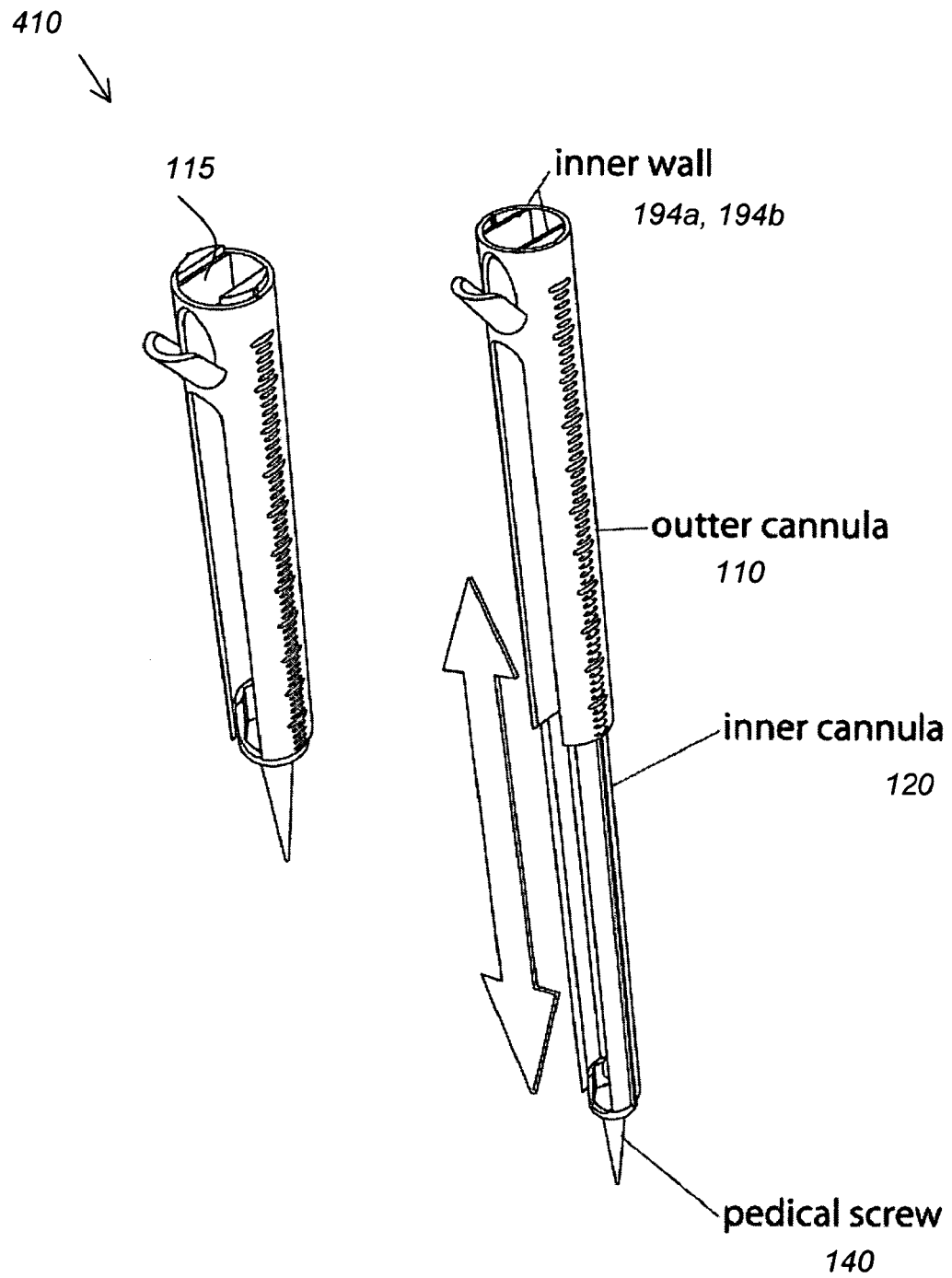
FIG. 18A is a perspective view of another embodiment of a portal with an adjustable length, according to this invention.
Figure 18B:
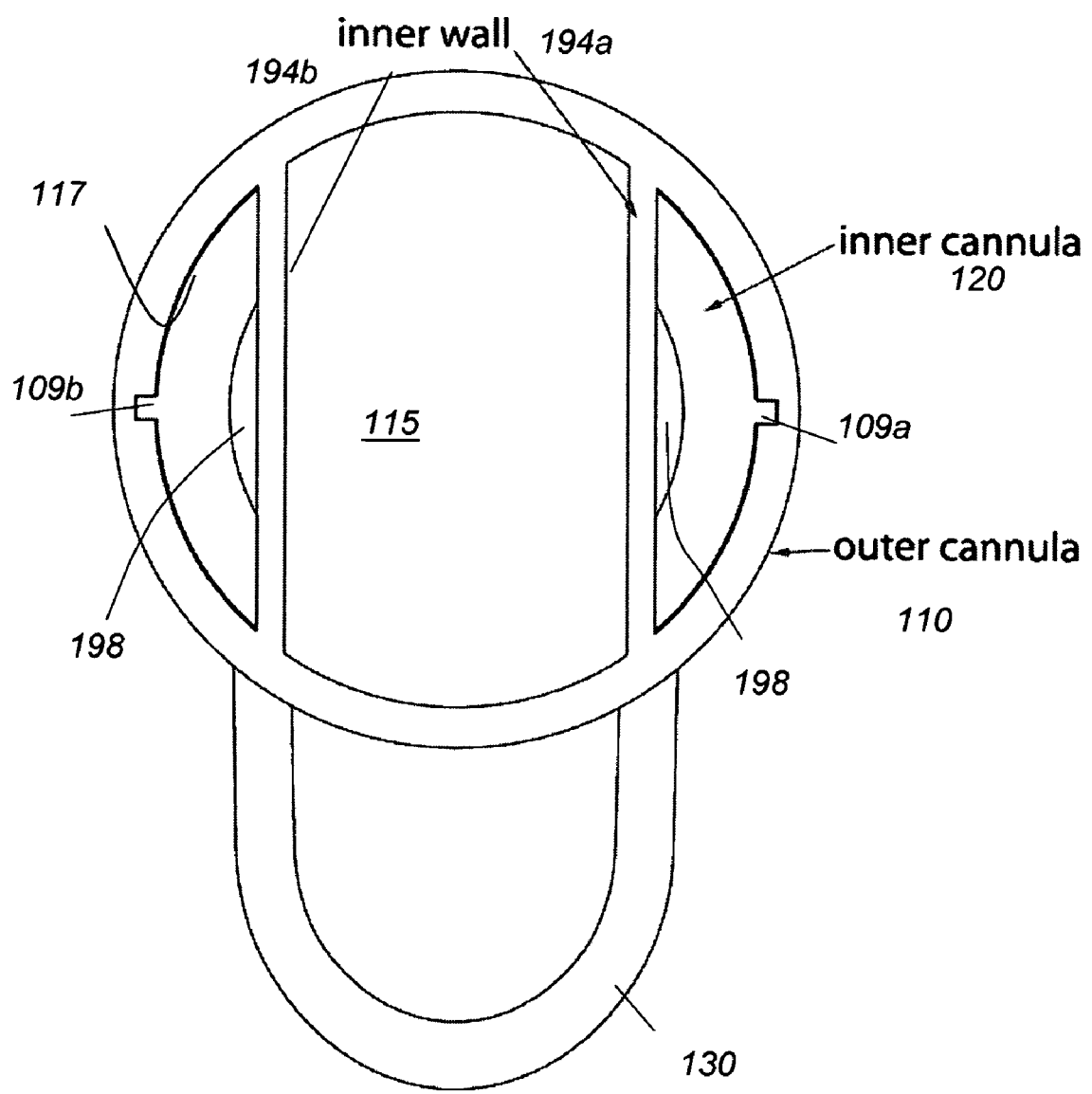
FIG. 18B is a top view of the embodiment of FIG. 18A.
Figure 19A:
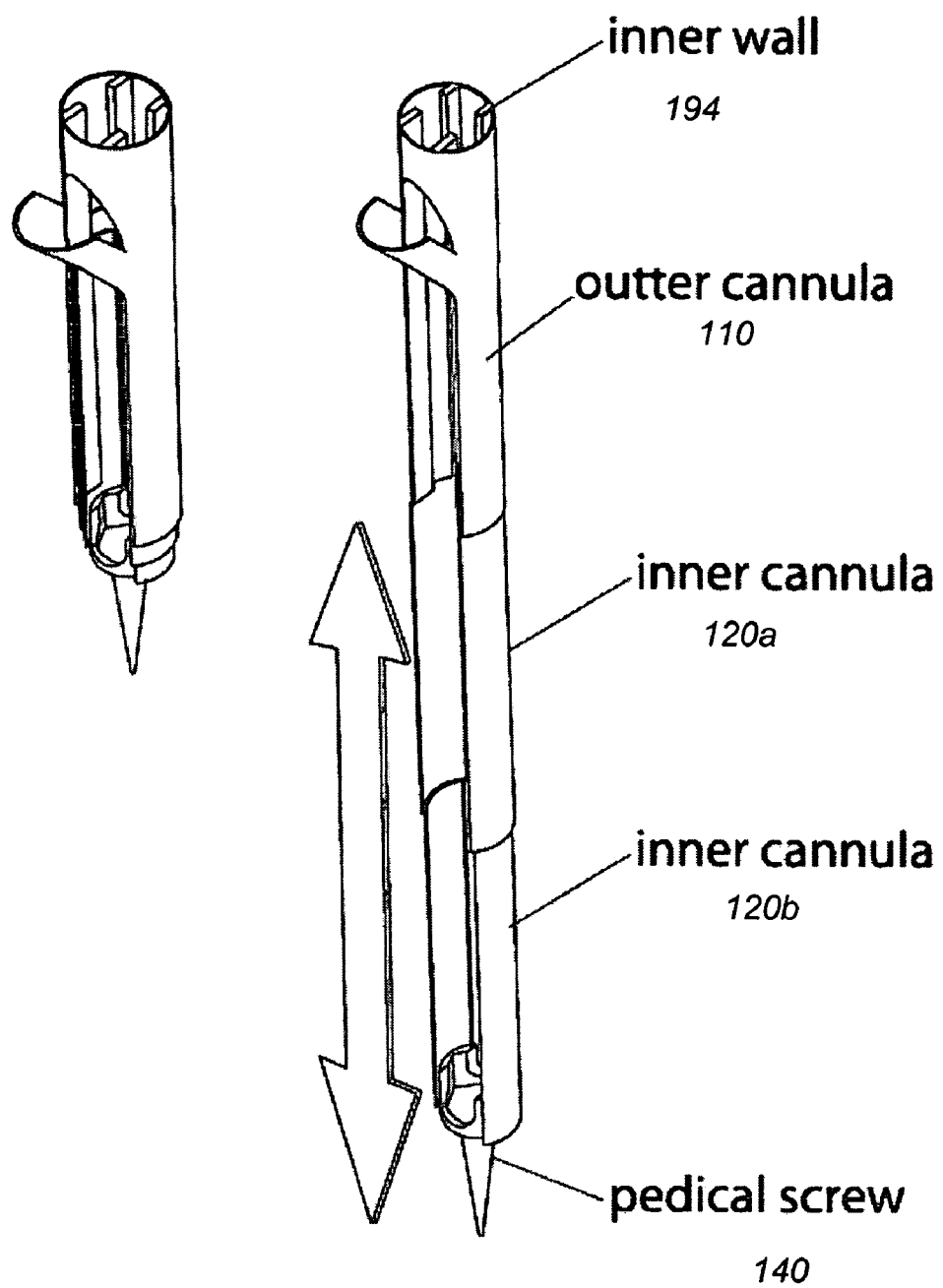
FIG. 19A is a perspective view of another embodiment of a portal with an adjustable length, according to this invention.
Figure 19B:
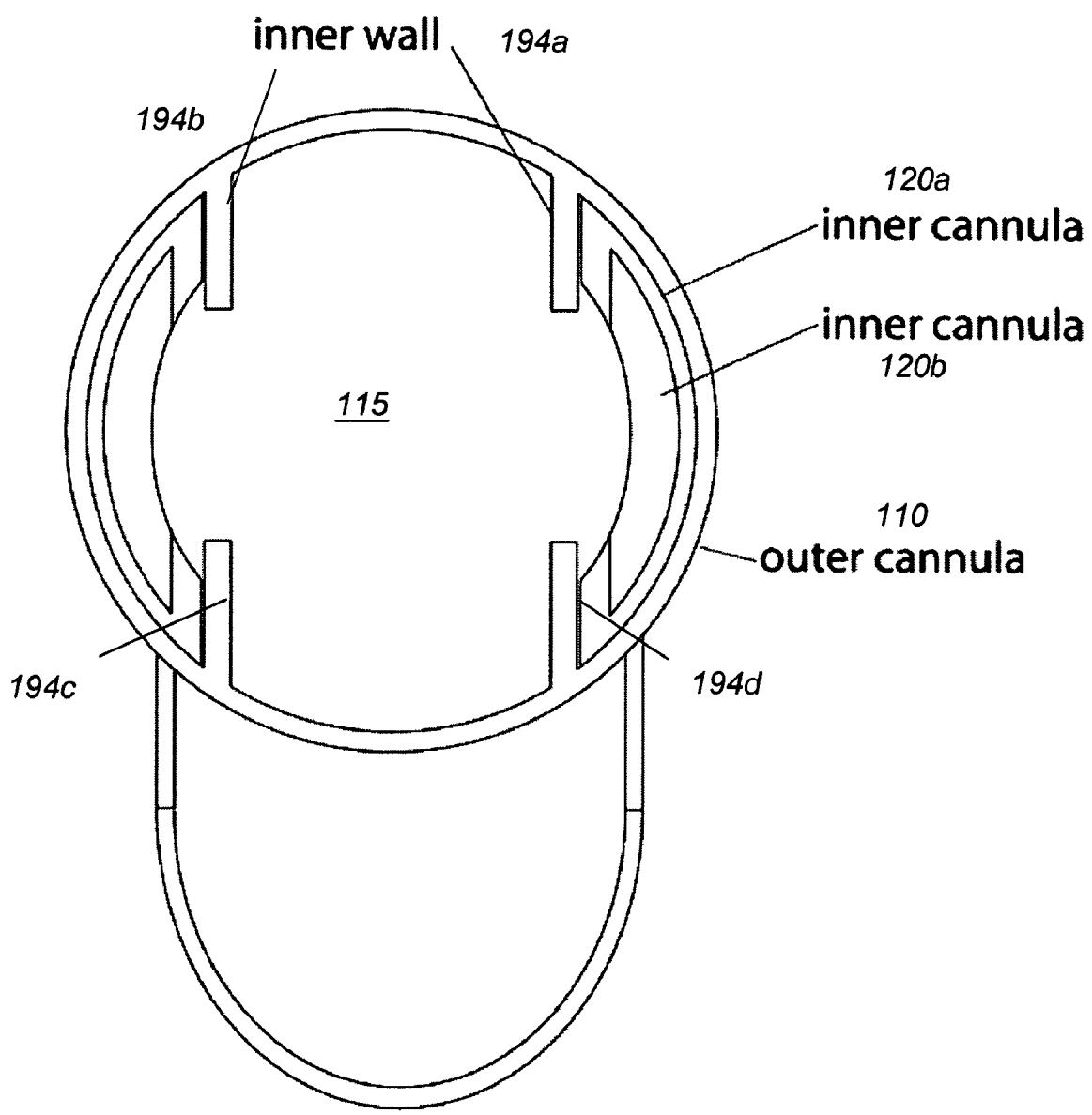
FIG. 19B is a top view of the embodiment of FIG. 19A.

Referring to FIGS. 18A and 18B, in another embodiment, the inner cannula 120 slides within a space 198 formed between the cylindrical inner wall 117 of the outer cannula 110 and two planar inner walls 194a and 194b extending from and connecting opposite sides of the cylindrical wall 117. In yet another embodiment, shown in FIGS. 19A and 19B, portal 420 includes an outer cannula 110 and two inner cannulae 120a and 120b. Inner cannula 120a slides against the inner cylindrical wall 117 of the outer cannula 110, against four planar walls 194a, 194b, 194c, of the outer cannula 110 and against the outer cylindrical wall of the inner cannula 120b. Inner cannula 120b slides against the inner cylindrical wall of inner cannula 120a.

Figure 20A:
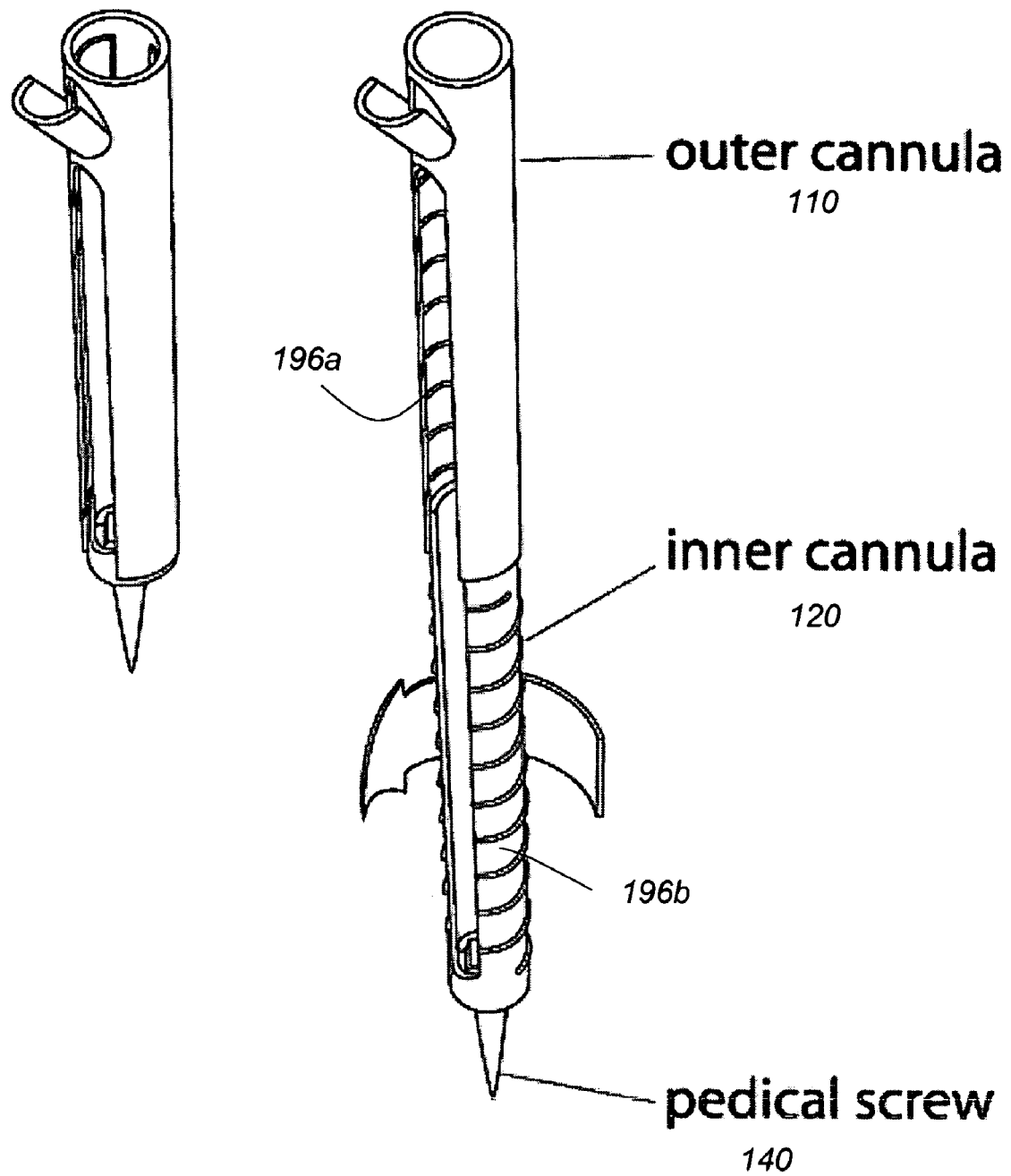
FIG. 20A is a perspective view of another embodiment of a portal with an adjustable length, according to this invention.
Figure 20B:
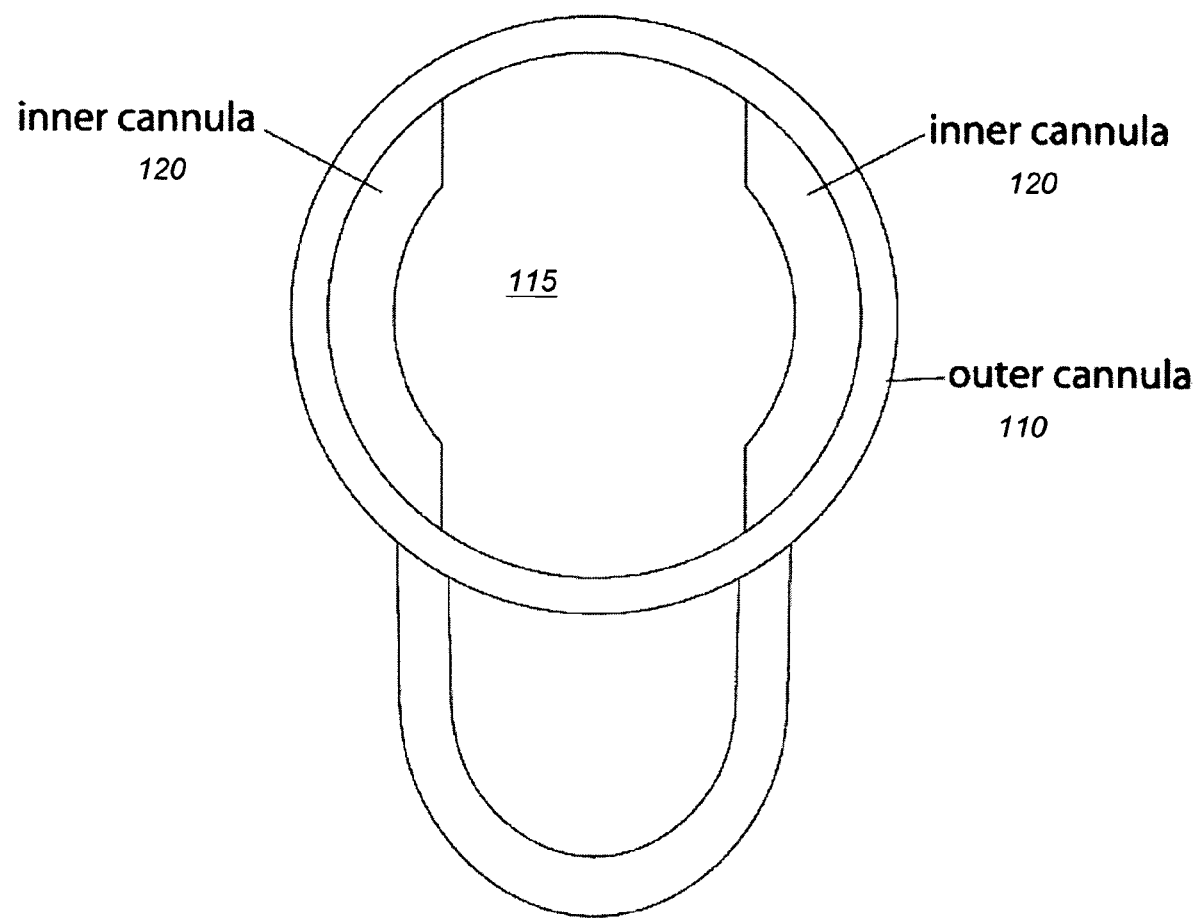
FIG. 20B is a top view of the embodiment of FIG. 20A.

In another embodiment the outer cannula 110 slides within the inner cannula 120 (not shown). In another embodiment, shown in FIGS. 20A and 20B, the portal 440 extends in a telescopic fashion as one piece. In this embodiment, the length is adjusted by unscrewing the outer cannula 110 or screwing the inner cannula 120 in each case relative to each other.

Figure 3A:
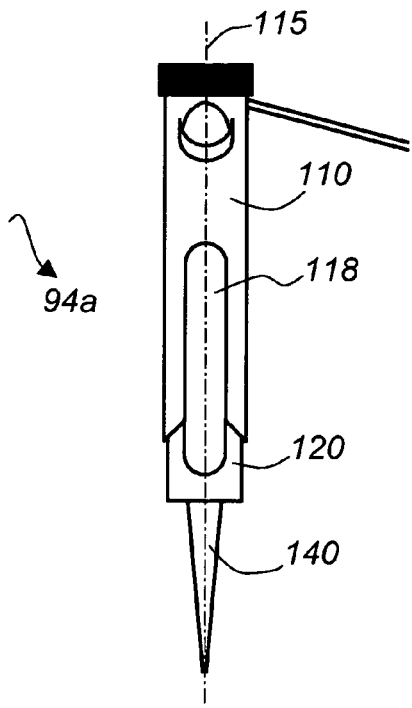
FIG. 3A-3C are perspective views of an assembled portal, according to this invention.
Figure 3B:
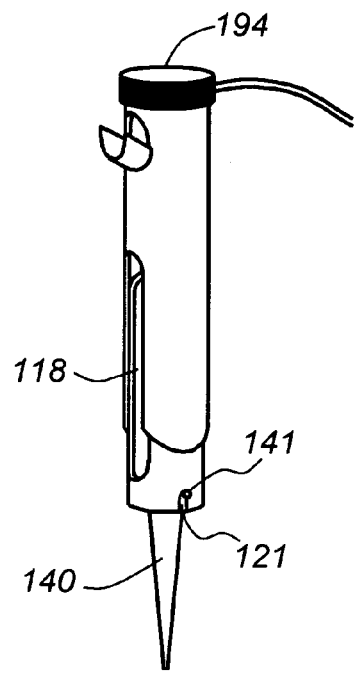
Figure 3C:
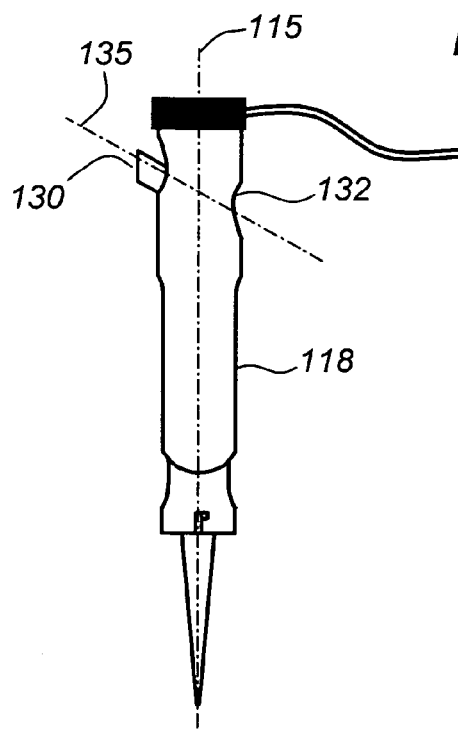

Referring to FIG. 3A, FIG. 3B, and FIG. 3C inner cannula 120 is rotated relative to the outer cannula 110 so that openings 118a and 118b are aligned, forming an elongated pass-through slot 118 when the portal 94a is assembled. Pedicle screw 140 includes an appendage 141 and is attached to the inner cannula 120 by engaging the appendage 141 to the outer cannula slot 121, as shown in FIG. 3B. In this embodiment access to the pedicle screw is achieved through the first working channel 115. In another embodiment the pedicle screw is engaged as an interference fit within the distal end of cannula 120. In either case a screw drive or pushing device fits into the head of the pedicle screw and stabilizes the screw, if the head is multiaxial, while it is being inserted deep into the body cavity.

Other instruments or devices may be inserted either through the first working channel 115 or the second working channel 135, shown in FIG. 3C. A detachable optical and/or illumination device 194 is interference fitted to the proximal end 112 of the outer cannula 110 and is capable of rotating around an axis passing through the first channel 115. The optical and/or illumination device may be a light source and/or an optical fiber that has one end connecting to a light source and a second end placed in the vicinity of the pathology area, thereby providing direct illumination and visualization of the pathology area. In other embodiments the illumination device may be fitted through the side portal 130 or through an inverted L-shaped appendage protruding from the inner wall of the outer cannula 110 into the first working channel and consisting of a hollow inner core that communicates with the inner and outer diameters of the outer cannula 110 and is sized to receive the optical device and/or the light source. Alternatively, the optical device may be similarly connected to inner cannula 120.

Figure 7:
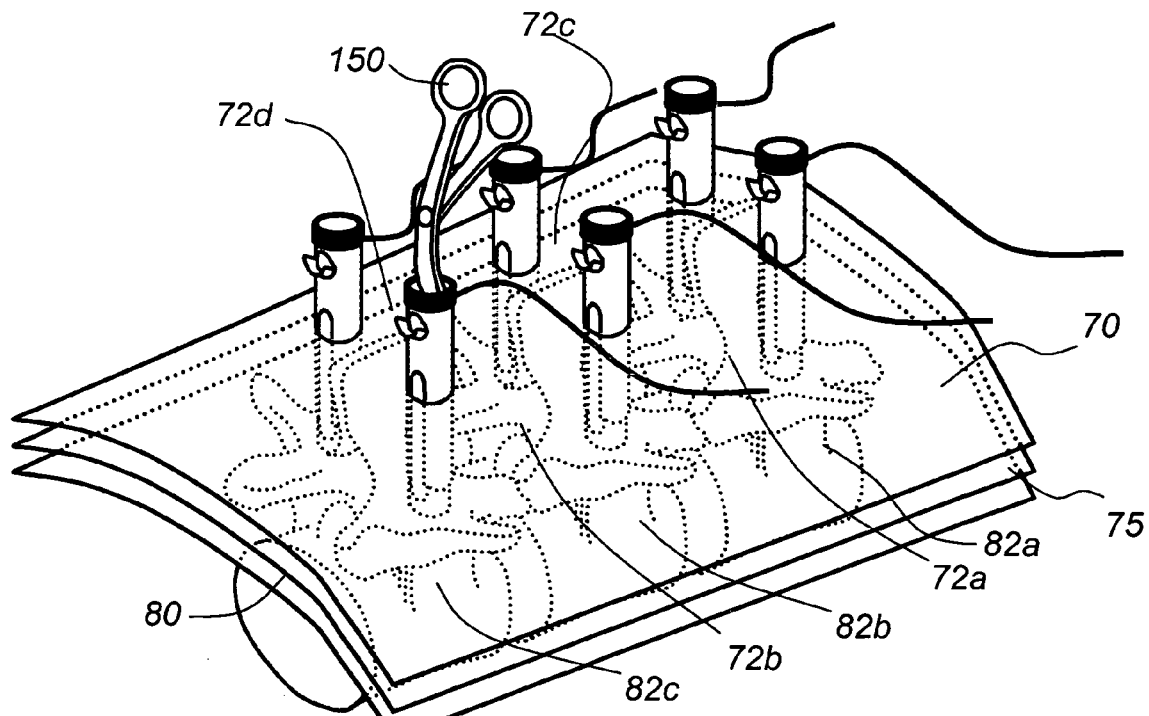
FIG. 7 is a top view of the patient's back as in FIG. 6 with a pair of curved scissors placed through a portal of this invention.

Customized instruments are also provided for insertion within the first working channel 115 or the second working channel 135. Referring to FIG. 7, a customized curved pair of scissors 150 is inserted through the first working channel 115 of portal 94c. In other embodiments scissors 150 are inserted through the side portal 130. Scissors 150 is used to incise the lumbodorsal fascia 75 in the area 72b between two adjacent portals 94c and 94b for opening a path 74b between them. This path 74b is then used for delivering and placing bone graft, connecting elements, such as rods, plates, wires, or articulating versions thereof, for connecting the adjacent vertebrae 82c and 82b of the spine 80. The connecting elements are then secured to the corresponding vertebrae 82c, 82b via screws placed through the first working channels 115 of the corresponding portals 94c, 94b. Similarly, paths 74a, 74c, 74d may be opened in the areas 72a, 72c, 72d between the adjacent portals 94b and 94a, 94d and 94e, and 94e and 94d, respectively. Other types of incision instruments may also be used, including curved scalpels, among others. In another embodiment, the curved scissors 150 is inserted through the working channel 135.

Figure 8:
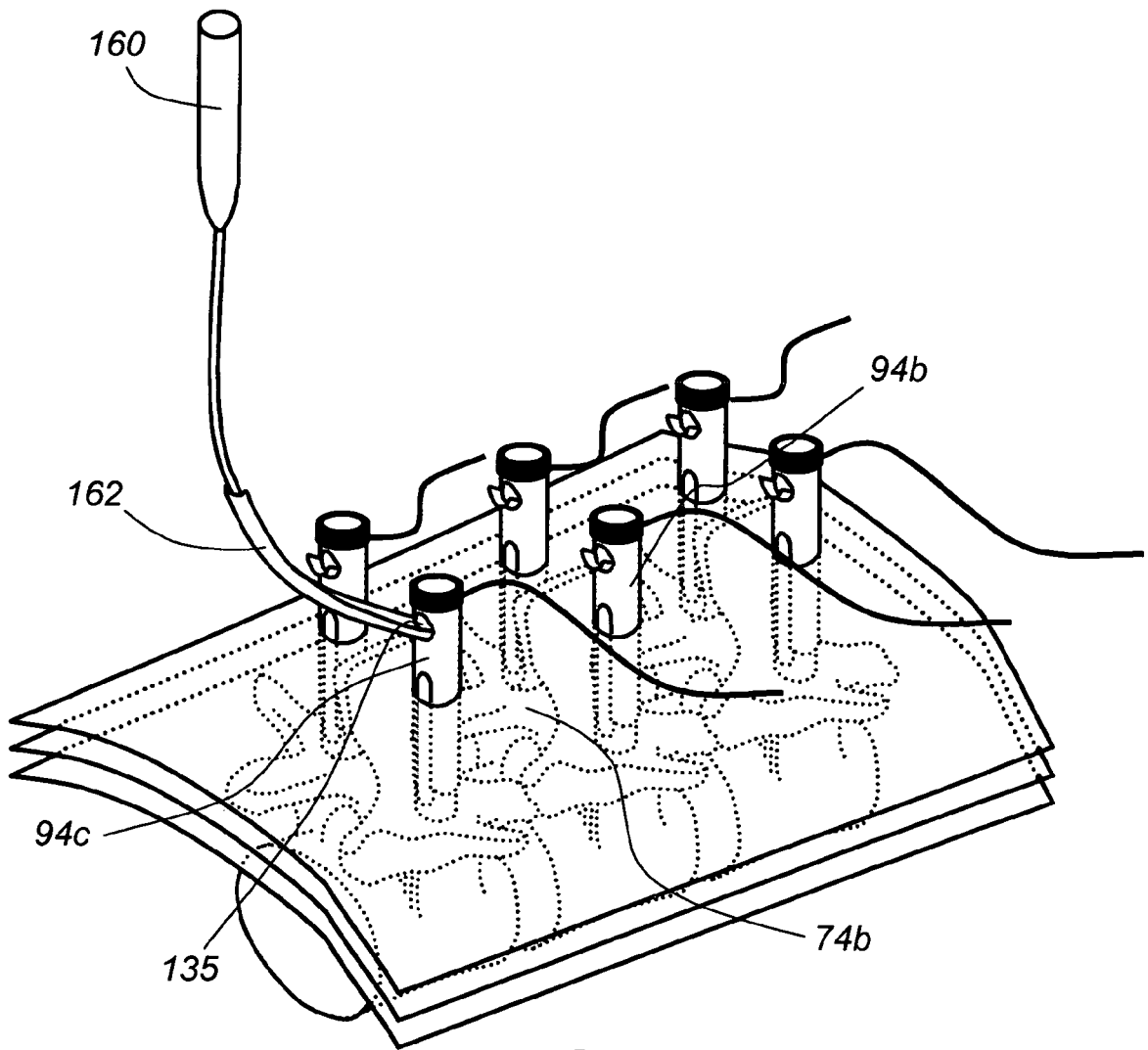
FIG. 8 is a top view of the patient's back as in FIG. 6 with a carrier device placed through a portal of this invention.
Figure 10:
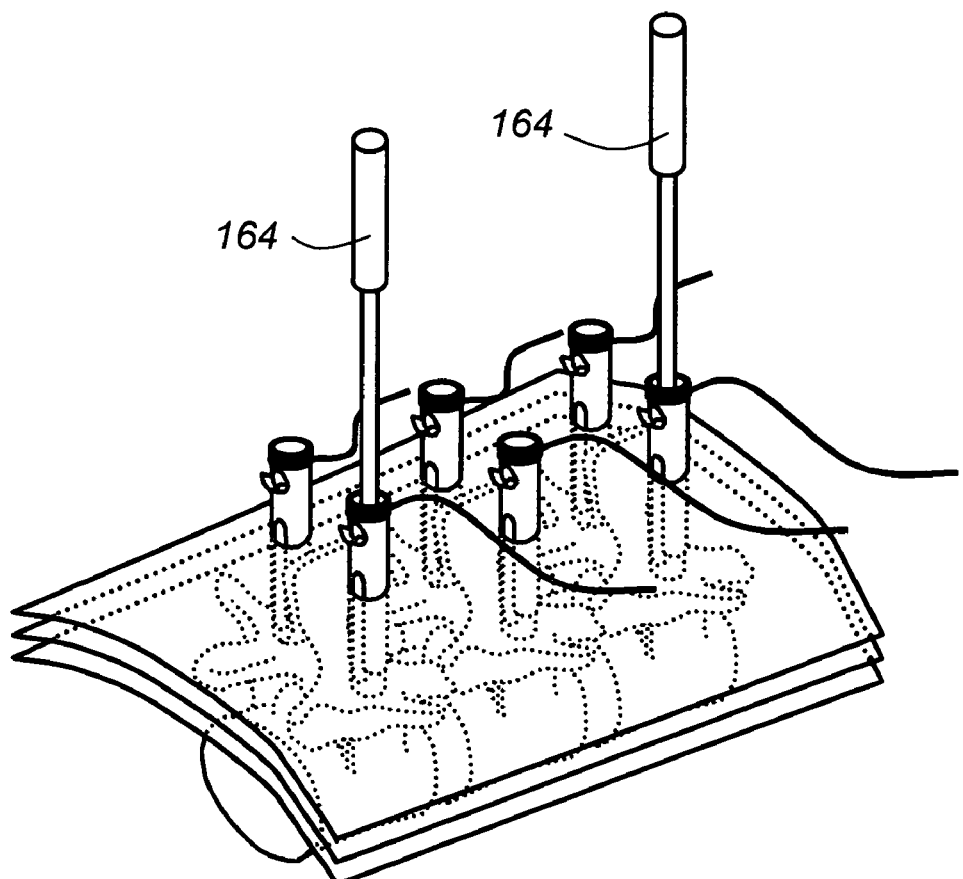
FIG. 10 is a top view of the patient's back with two rod carrier devices placed in two different portals for inserting an entire rod in the area between the two portals, under the skin and lumbodorsal fascia and attaching it to the connection points.
Figure 21:
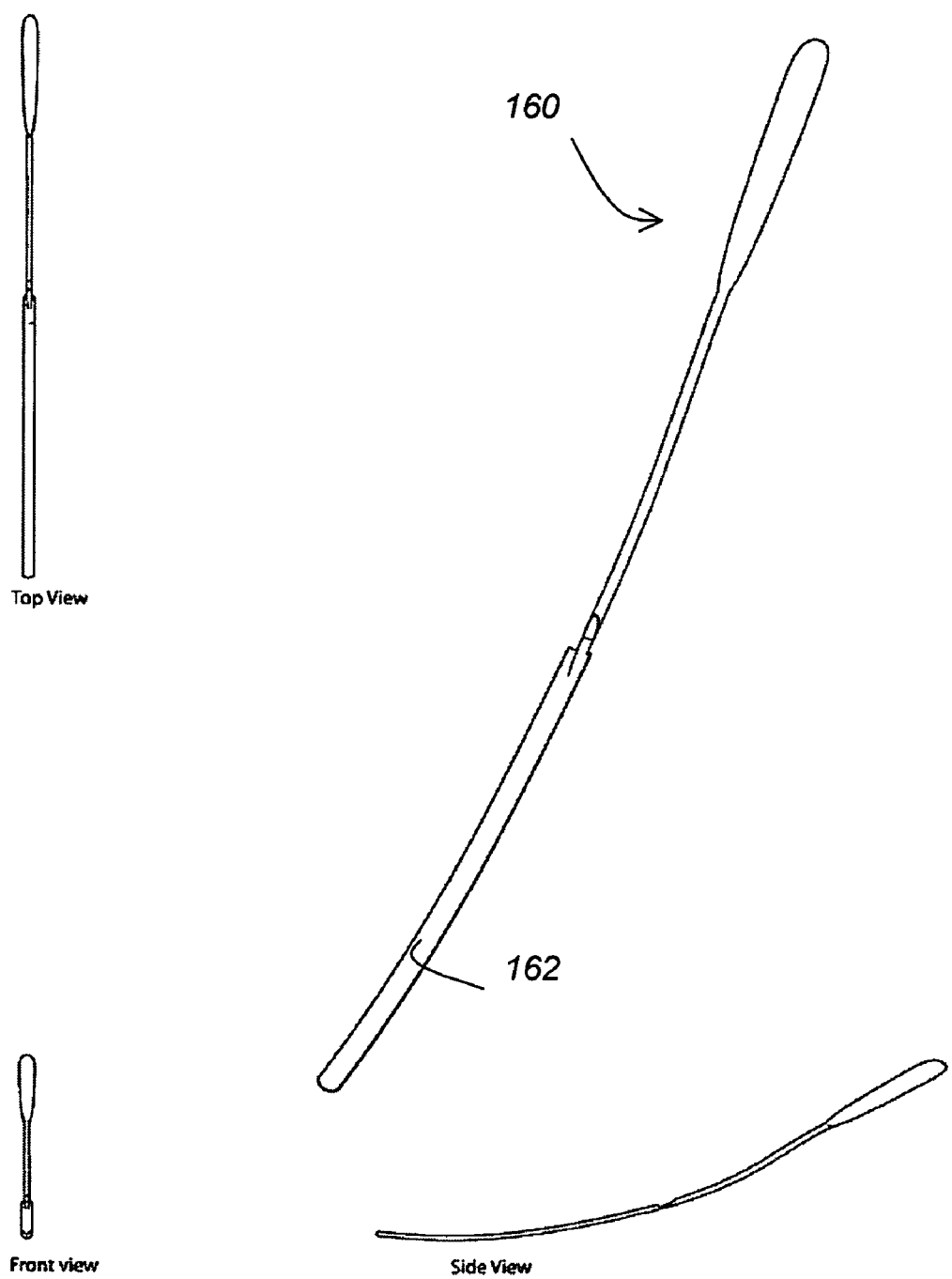
FIG. 21 depicts a perspective view, a top view, a front view and a side view of a carrier device.

Referring to FIG. 8, FIG. 9, and FIG. 21, a customized curved carrier instrument 160 is inserted through the opening of the second working channel 135 of portal 94c and passes through the opened path 74b between the adjacent portals 94c, 94b. Instrument 160 enters the first working channel of portal 94b through the side slot 118. Instrument 160 is used for delivering the above mentioned bone graft, connecting elements 170, screws or biological materials in the areas between the adjacent portals. The front portion 162 of the carrier instrument 160 includes an elongated semi-cylindrical groove for carrying the connecting elements 170. In another embodiment, the front portion 162 may be a cylindrical tube as one piece or two separate pieces which can rotate relative to each other to form a cylinder or a half cylinder, shown in FIG. 9A and FIG. 9B. The tip of the carrier instrument 160 may be shaped as the tip of a bullet or a canoe to shield the devices being carried from the surrounding soft tissues as the carrier device is forced through the tissues between the adjacent portals 94c, 94b. The carrier instrument 160 may be flexible, malleable, or rigid and may be expandable at body temperature.

Figure 14:
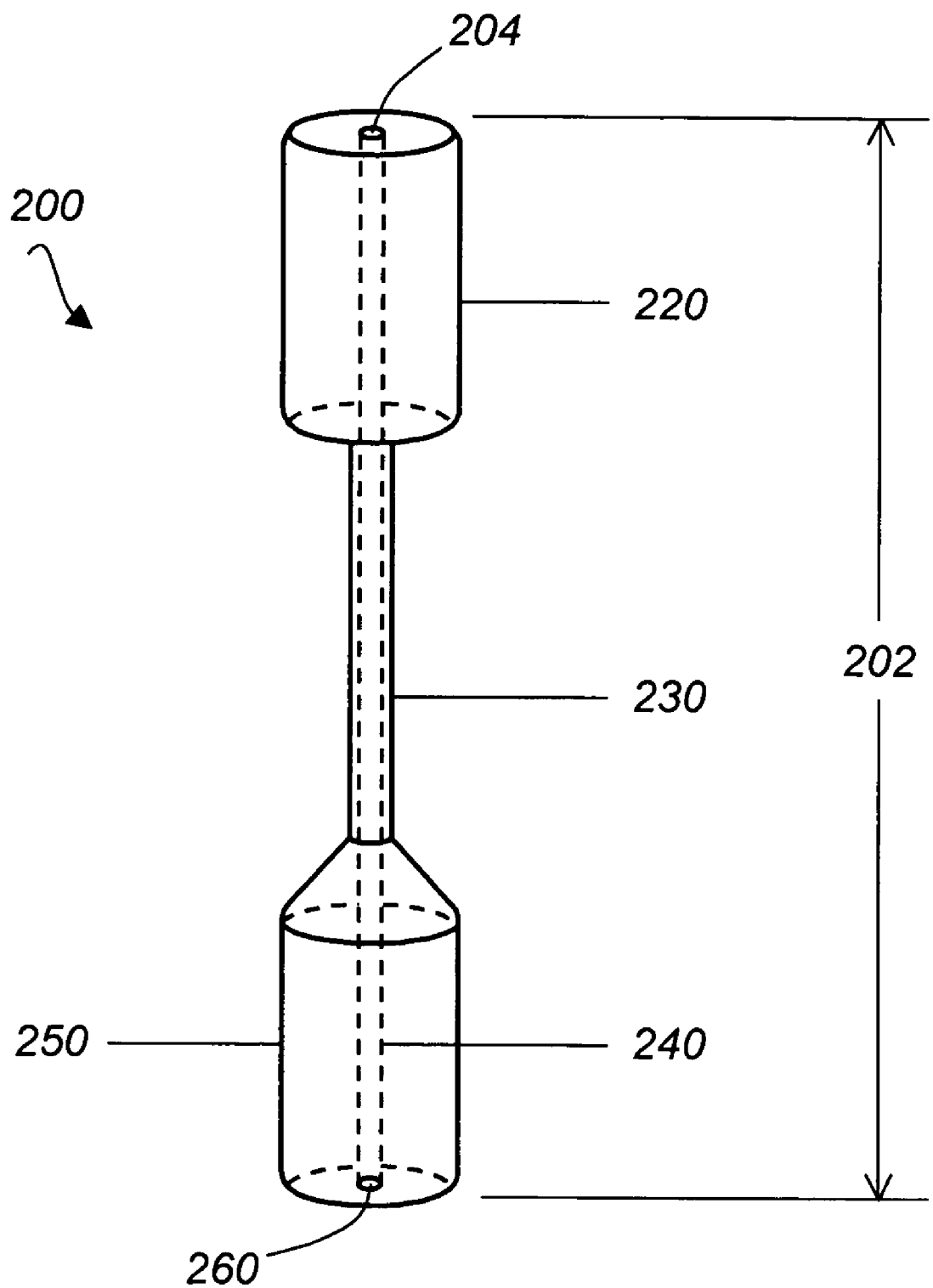
FIG. 14 is a front view of a cannulated tissue dilator that when rotated creates a cylindrical space along its path.

Referring to FIG. 14, a customized tissue dilator instrument 200 is provided for developing a path in the soft tissues from the skin surface 70 of the patient's body 90 to a desired depth within the patient's body. Instrument 200 includes a handle 220 that connects to a shaft 230 and the shaft 230 connects to a paddle 250. An elongated cannula 240 extends the entire length 202 of the instrument 200 and connects an opening 204 at the proximal end of the handle to an opening 260 at the distal end of the paddle 250. By rotating the paddle either clockwise or anticlockwise and moving up or down from the skin 70, respectively, to the deeper layers, a cylindrical path is created with diameter equal to the width of the paddle 250.

Figure 15:
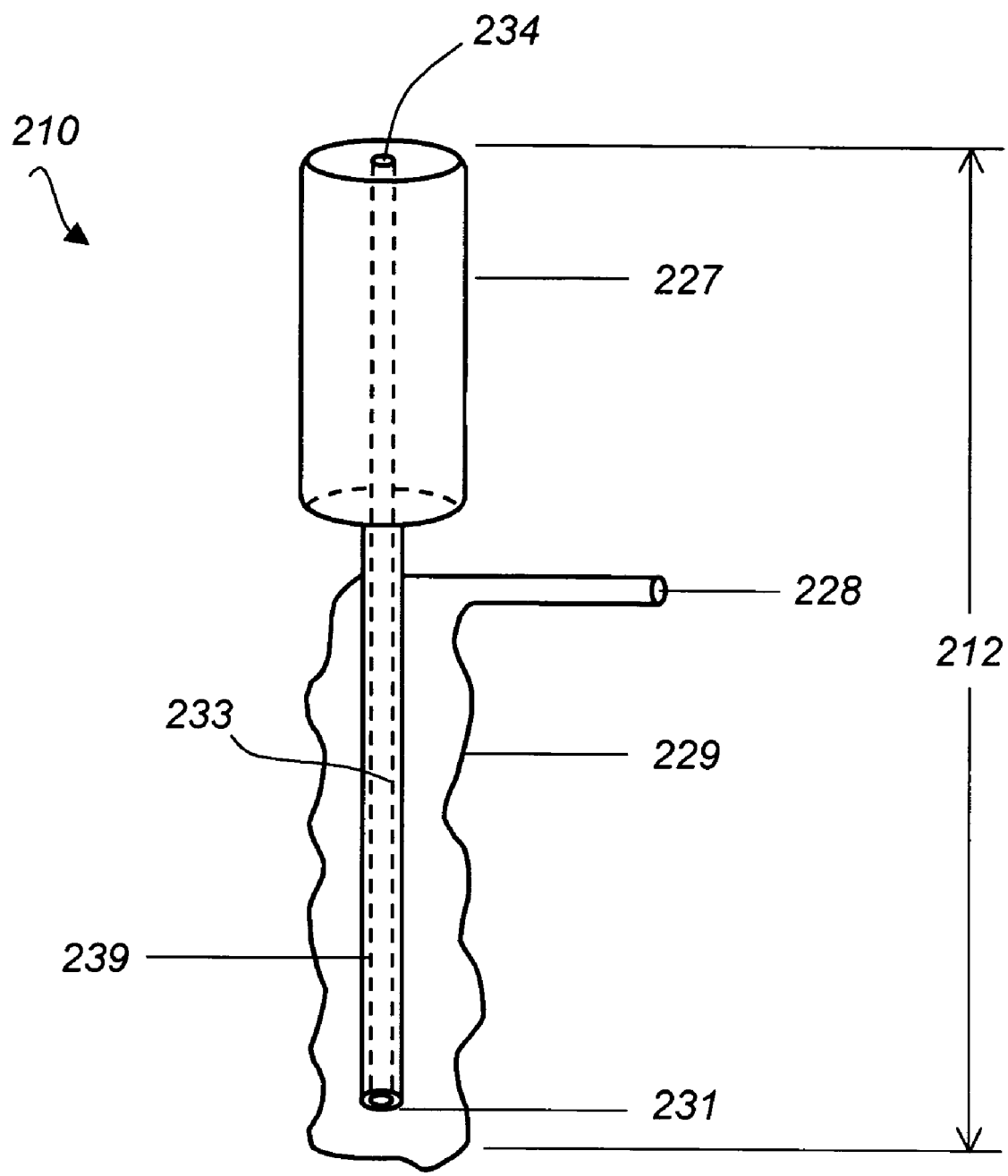
FIG. 15 is a front view of a collapsible tissue dilator that can be inflated to create a space along its path.

Referring to FIG. 15, another customized tissue dilator instrument 210 is used for developing a path in the soft tissues from the skin surface 70 of the patient's body 90 to a desired depth within the patient's body and for removing the soft tissues along the opened path. Instrument 210 includes a handle 227 that connects to a shaft 232 having a cannula 233. Cannula 233 extends the entire length of the instrument 212 and has a proximal opening 234 and a distal opening 231. Shaft 232 is surrounded by an inflatable balloon-type component 229 which when inflated through a connected tube 228 and moved up and down from the surface 70 to the deeper layers, clears a cylindrical space in the soft-tissues along the path of the instrument equal in diameter to the largest diameter of the inflated component 229.

Figure 4:
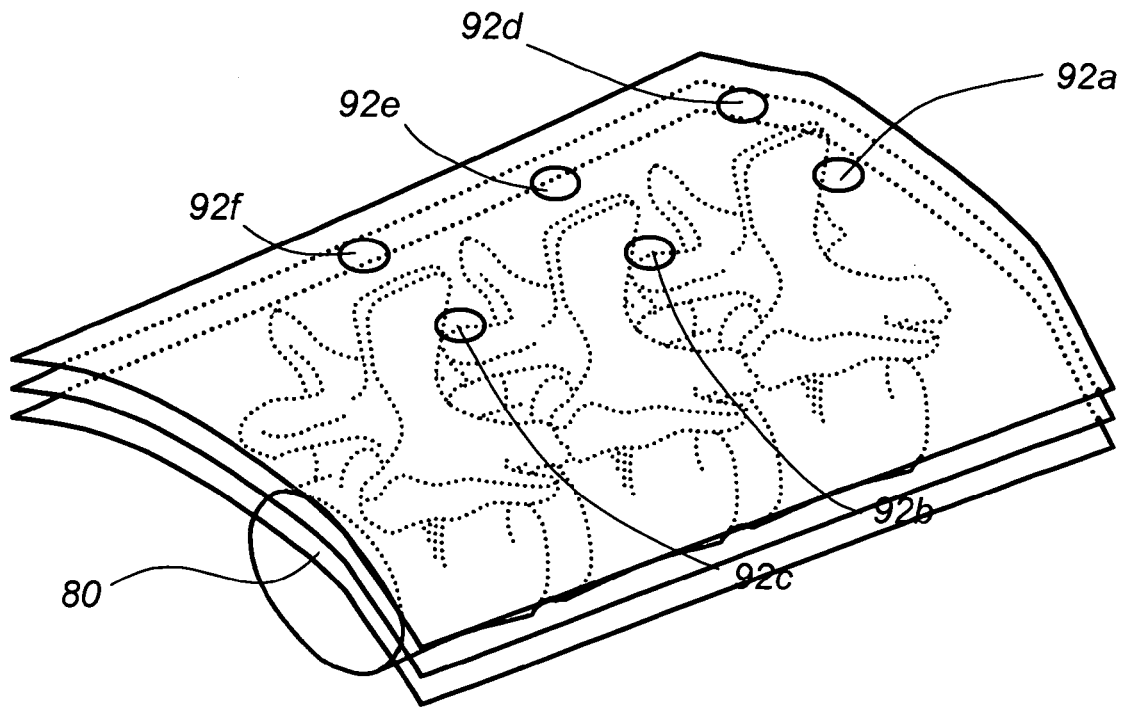
FIG. 4 is a layered top view of the patient's back with incisions made on the skin extending through the lumbodorsal fascia to the deep tissues.
Figure 5:
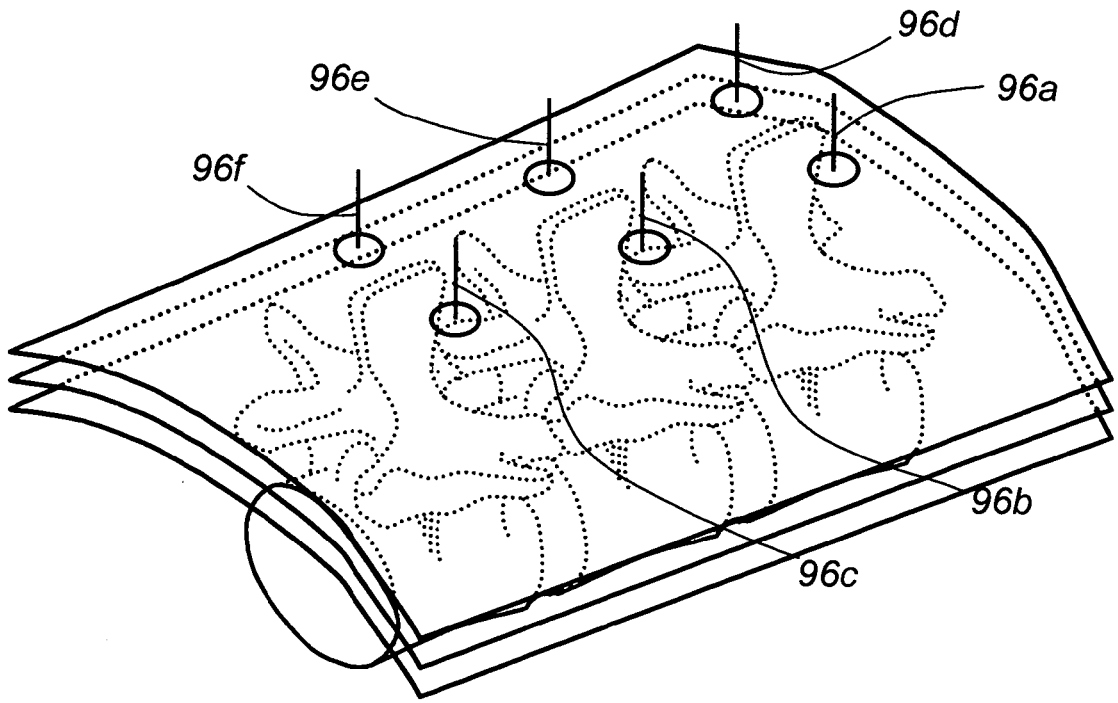
FIG. 5 is a layered top view of the patient's back with incisions made on the skin and guide wires placed percutaneously through the skin and into the underlying vertebrae.
Figure 6:
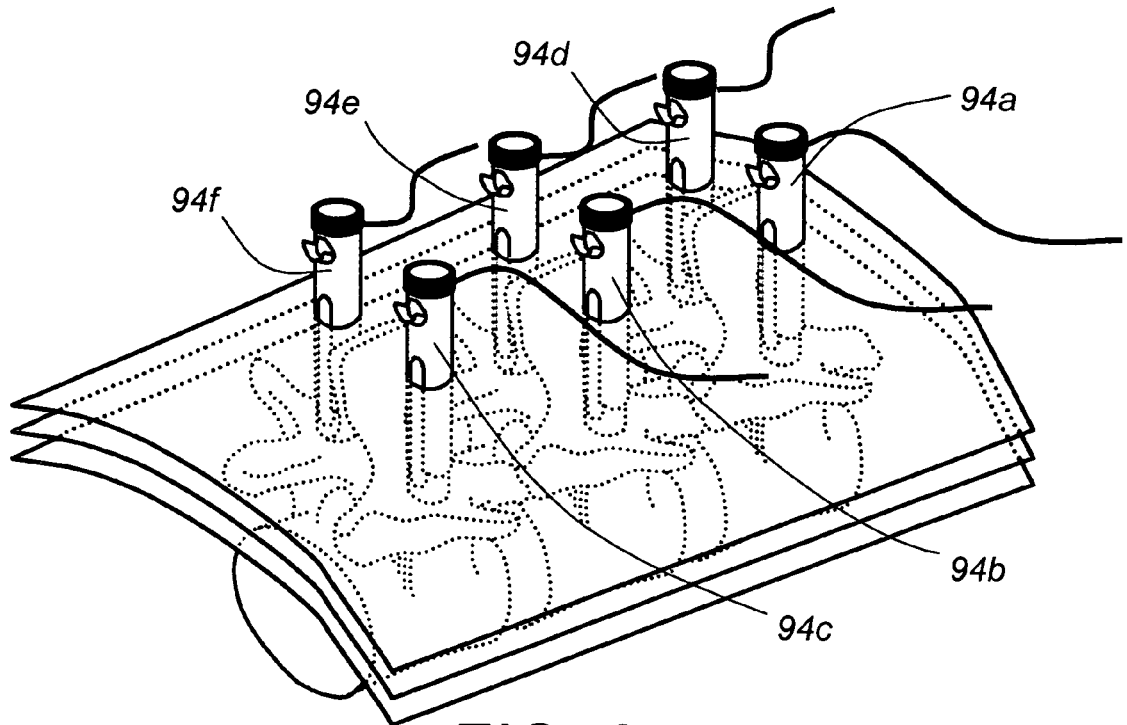
FIG. 6 is top view of the patient's back with portals placed in the openings formed from the skin surface and extending deep into the pathology areas.
Figure 11:
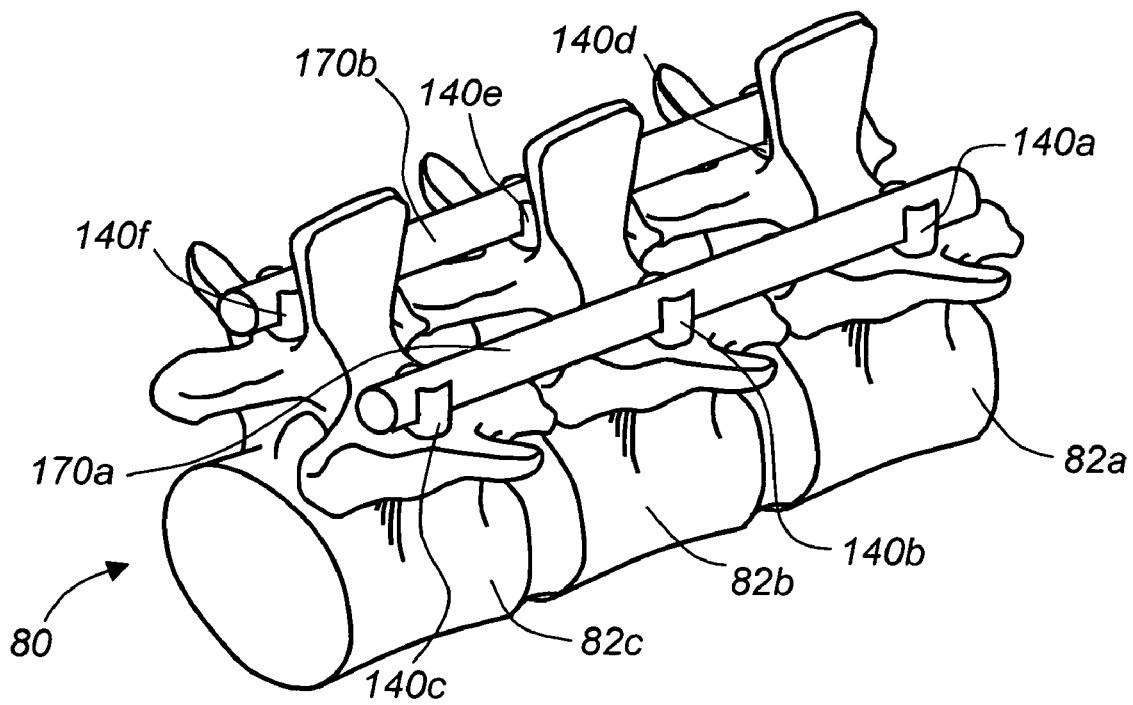
FIG. 11 is a top view of a connecting rod that was placed in the slots of three sequential pedicle screws using the portals of this invention.
Figure 12:
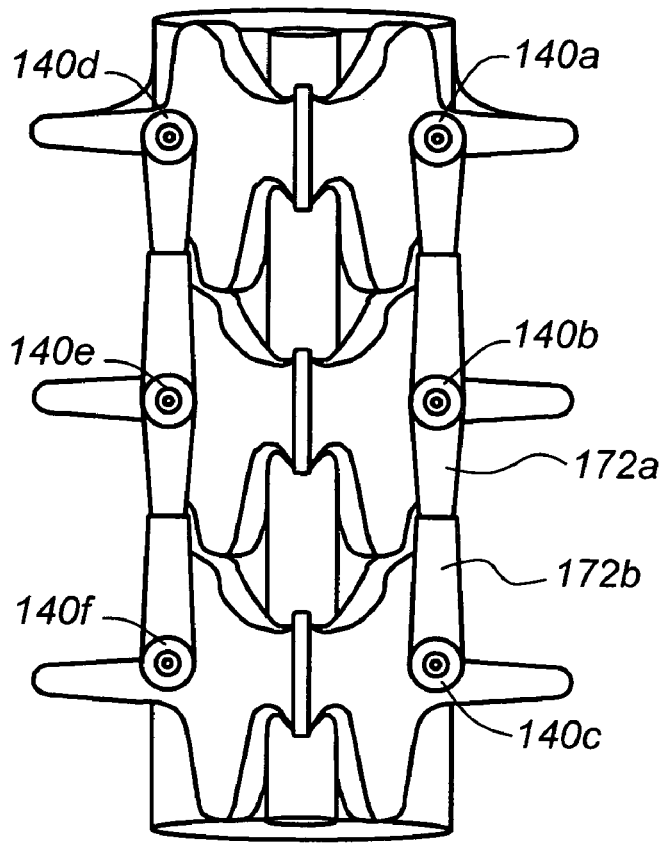
FIG. 12 is a front view of a connecting articulating device that was connected to three sequential pedicle screws using the portals of this invention.
Figure 13:
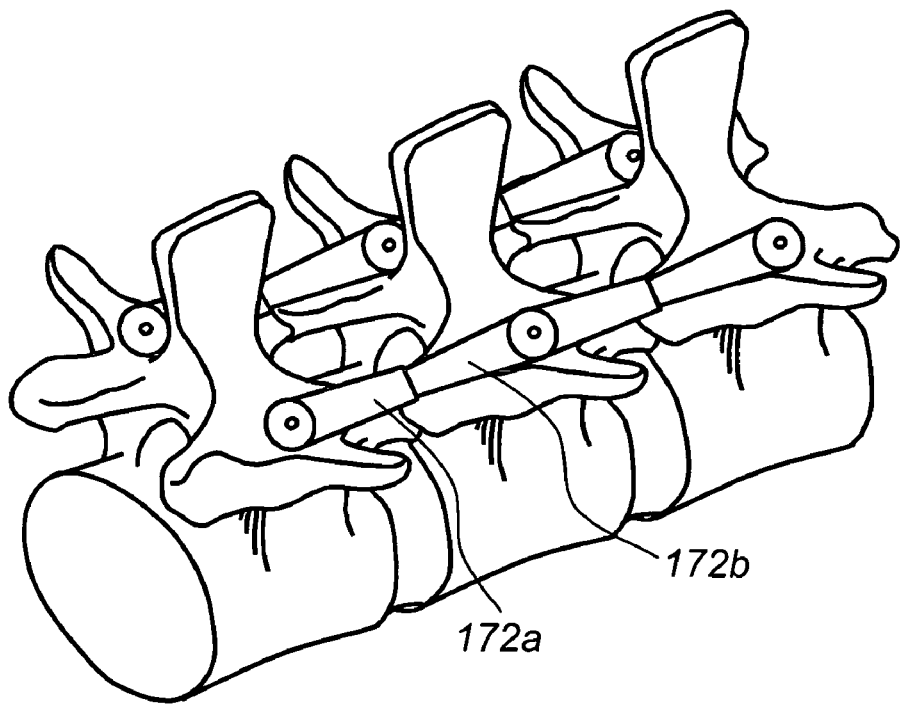
FIG. 13 is a perspective view of a connecting articulating device that was placed under the skin and lumbodorsal fascia and was connected to three sequential pedicle screws using the portals of this invention.
Figure 16:
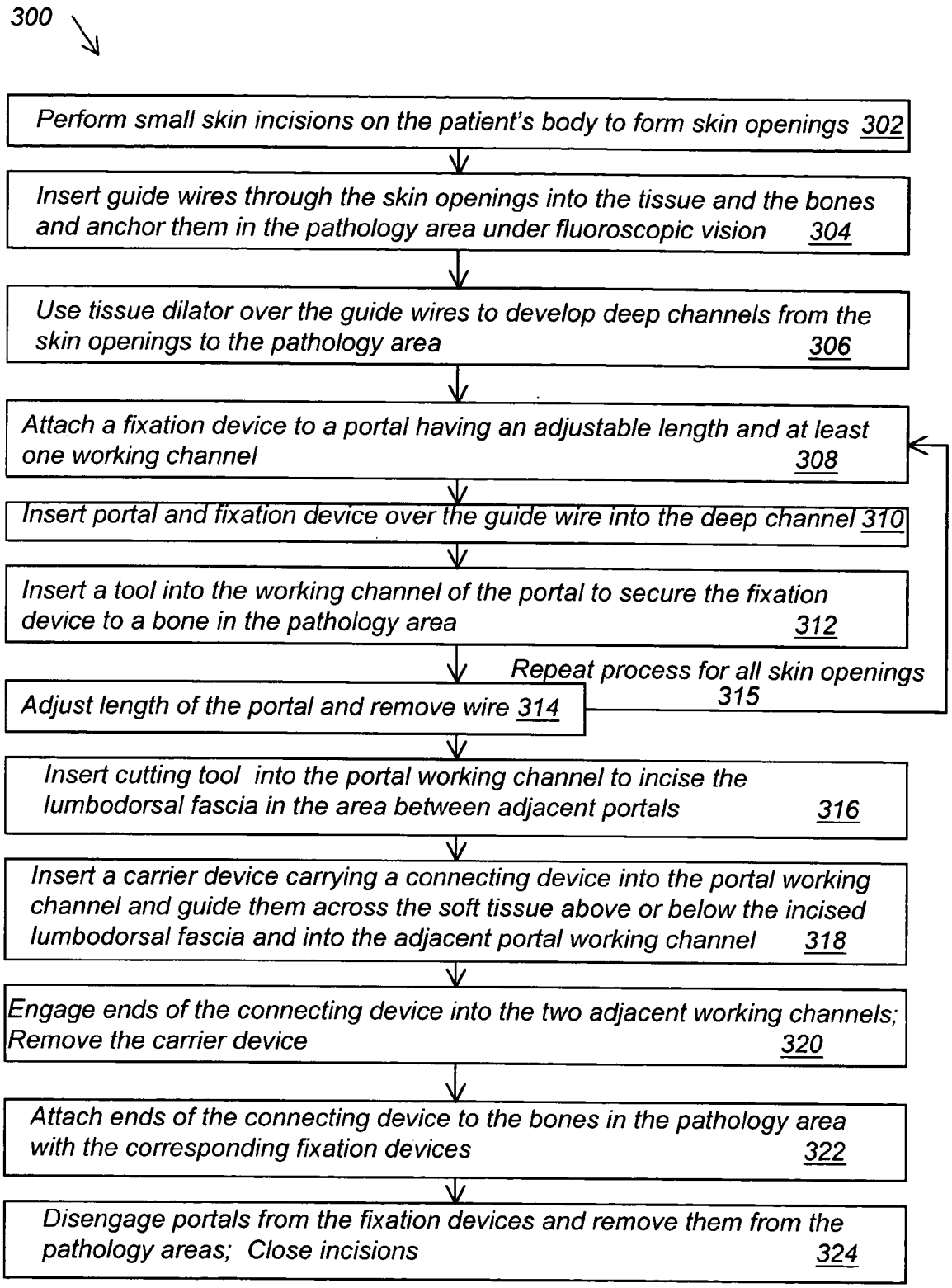
FIG. 16 is a block diagram of a spinal operating procedure utilizing the portals of this invention.

The steps of a spinal surgical procedure 300 in accordance with one aspect of the present invention are depicted schematically in the block diagram of FIG. 16 and figuratively in FIG. 1 to FIG. 15. The present embodiment of the invention permits a substantially mid-line or medial posterior or postero-lateral approach to the spine but other approaches to other parts of the body are understood to be feasible with this invention. Referring to FIG. 16, FIG. 1 and FIG. 4, in a first step of the technique, small incisions are made in the patient's skin 70 along the spine 80 creating skin openings 92a-92f (302). Next, guide wires 96a-96f are advanced through the skin openings 92a-92f, respectively, through the underlying tissue and into the bony anatomy of a vertebral element such as a pedicle (304). The wires are inserted under fluoroscopic vision or as an open procedure under direct vision. In the subsequent step, a tissue dilator as depicted in FIG. 14 and FIG. 15 is advanced over the guide wires (306). The dilator is either inflated (as in FIG. 15) or rotated (as in FIG. 14) and withdrawn slowly to develop a channel from the skin to the fixation point of the guide wire. In the next step, a fixation device such as a pedicle screw 140 is attached to each of the working portals 94a-94f and secured via the locking mechanism 141, as depicted in FIG. 2A and FIG. 3A (308). A cannulated screwdriver or an elongated instrument is connected to the fixation device 140 and combined with the portal assembly is advanced through the incision (312). The portal assemblies 94a-94f including the pedicle screw 140 and screwdriver are inserted over the guide wires 96a-96f, respectively, and into the bone as depicted in FIG. 6 (310). Alternatively, a second tissue dilator having a cylindrical shape similar to the portal assembly but with a larger diameter and with an opening slot running unilaterally along its entire length may be inserted through the skin opening and left in place so that the portal assembly can be inserted inside of this second dilator thereby preventing tissue being caught within the portal assembly. The second dilator can then be removed when the portal assembly is inserted by sliding the second dilator around the portal assembly via the opened channel. Once the working portals 94a-94f rests against the patient's skin 70, the cannulae 110 and 120 will start to slide with respect to each other as the fixation device 140 advances through the soft tissues until the desired depth is reached (314). This is a unique feature of this invention that will significantly improve the ease of performing percutaneous surgery since there is no need to replace the fixed length portals to achieve the right depth into the patient's body or attach other cannulae to increase the length of the main working channel. In cases of thin patients portals with fixed length usually protrude high above the level of the patient's skin and require external support for stability. This invention does not require an external support for the portal because the length of the protruding portal is always constant because the portion beneath the skin is adjustable. However, an external support may be attached to either the main portal or the side working portal for added stability. Once the portals are in position, the guide wires 96a-96f are removed (314). The above steps are repeated for as many pedicle screws and openings that are required (315). A pair of curved facial scissors 150 or curved scalpel is then inserted through the working channel 115 of portal 94c or through channel 135 of side portal 130 and advanced beneath the patient's skin 70 while cutting through the lumbodorsal fascia 75 until the scissor tips enter the next adjacent portal 94b through the slot 118, as in FIG. 9 (316). At this point the lumbodorsal fascia is completely discontinuous in the area 72b between the two portals 94c and 94b. A carrier device 160 is then inserted through channel 135 of side portal 130 across the soft tissues either above or below the level of the lumbodorsal fascia 75 until the tip of the carrier enters the next adjacent portal 94b (318). The carrier device 160 has a semi-cylindrical front portion 162 that is used to support various objects that need to be inserted into the pathology areas. In the example of FIG. 9, a connecting device 170, such as a cylindrical rod, plate, articulating device, or biologic substances is placed in the semi-cylindrical front portion 162 either before insertion or after insertion and is brought in the tissue area between portal 94c and 94b. In other examples, the front portion 162 has a full cylindrical shape or includes two semi-cylindrical segments 162a and 162b that can open or close to form either an open semi cylinder or a closed cylinder, as shown in FIG. 9A and FIG. 9B, respectively. This step can be repeated between multiple adjacent portals or across sets of portals for segmental fixation as shown in FIG. 11, FIG. 12 and FIG. 13. After the connecting device 170 is engaged within the portals, the carrier device 160 is retracted from the portals and the connecting device 170 is then inserted to the base of the portals or until it engages the fixation elements 140, such as a pedicle screw, as shown in FIGS. 11-13 (322). Pushers 164 are available to apply force to the connecting device 170 as it advances through the soft tissues. This technique allows the connecting device 170 to approach the fixation points in a direct fashion rather than indirectly at an angle or indirectly via a predetermined arc. This technique also only uses direct vision at the fixation points while not seeing the portion of the connecting device between the fixation points. This diminishes the size of the soft tissue dissection and trauma as well as the incision size. Once the connecting device is engaged to the fixation points, locking screws are then used to secure the connecting device to the fixation points (322). The main tube is pushed downwards and turned counterclockwise or clockwise to disengage the appendage 141 from the slot 121 (324). It is understood that the slot may be vertical only or horizontal only or a combination of the two or other configurations not specified in this invention. The tube is then removed from the incision and the incision closed in a standard fashion (324).

One of the unique features of this invention is the ability to engage and disengage the portals to and from the fixation devices 140, respectively, at any point during the operating procedure. In one example, the dilator device of FIG. 15 is placed in the depth of the incision and inflated to reopen the path to the fixation device 140. The portal 94a is replaced over the fixation device 140 and engages the appendage 141 on the fixation device 140, which in this case is a locking screw. The locking screw is then removed. This process is then repeated for as many fixation points as necessary. The connecting device 170 is either advanced laterally to disengage one or more fixation points 140a-140c or it is grasped at each fixation point under direct vision and advanced upwards. The carrier 160 is then advanced beneath one end of the connecting device 170 and then the connecting device is grasped at that end and pulled diagonally along the carrier 160 out of the incision through the end of the working portal 94b. With the portals engaged the procedure can be repeated from any point according to the sequence described above.

Once the main assembled portals are fixed to the appropriate depth, an optic and or illumination device 194 can be connected at varying locations on cannula 110, 120 or working channel 135. In one specific embodiment, the optic or illumination device is most preferably a fiber optic, although a rod lens scope or other viewing scopes may be utilized.

Because the portal is freely situated within the patient's skin and soft tissues, it can be manipulated to be centered over the target region. Repositioning of the portal can be performed manually under fluoroscopic guidance or be fitted with a position sensing devices, such as LEDs, in order to be guided stereotactically. Once the portal is appropriately positioned a variety of procedures using a variety of instruments can be performed through the main working channel 115 or the side channel 135. It is understood that these various tools and instruments are designed to fit through the working channels. For instance, in one specific embodiment, the working channel 115 through the cannulae 110 and 120 have a maximum inner diameter of 13 mm and the working channel 135 a maximum diameter of 10 mm. The present invention is not limited to the diameters mentioned for the working channels, since the dimensions of the components will vary depending upon the anatomy of the surgical site and the type of procedure being performed and as such the channels will vary.

While the present invention permits the surgeon to conduct surgical procedures in the working channels under a dry environment, irrigation may be provided separately through the working channel 135 to keep the visualization space clear. Separate or combined irrigation and aspiration elements can also be inserted through the working channel 135 or the main channel 115 as required by the procedure. In another embodiment the irrigation and aspiration elements may be combined with the optic and or illumination assembly or some combination thereof.

Other embodiments are within the scope of the following claims. For example, the cannulae may have other cross-sections such as rectangular or square. The cannulae may be flexible or semi rigid. The devices may be made of metal such as stainless steel, titanium, plastic, rubber, graphite, glass, expandable materials under body temperature, or other radiolucent materials.

Several embodiments of the present invention have been described. Nevertheless, it will be understood that various modifications may be made without departing from the spirit and scope of the invention. Accordingly, other embodiments are within the scope of the following claims.

What is claimed is:

1. A system for providing access to a spine of a patient, the system comprising:
   a first cannula comprising a proximal end and a distal end insertable into the patient proximate the spine, the distal end comprising a docking element shaped to mate with a first connecting element implantable in a first vertebra of the spine, the first cannula further comprising a first slot portion formed in a side wall of the first cannula, the first slot portion having a longitudinal axis, and a feature longitudinally aligned with the first slot portion on the longitudinal axis of the first slot portion, the first cannula further comprising a second slot portion arranged diametrically opposed to the first slot portion to permit passage of a spinal fusion rod through the first cannula along a direction transverse to a central axis of the first cannula;
   wherein the feature is separated from the first slot portion by an intervening element spanning a region substantially between the first slot portion and the feature;
   wherein, upon implantation of the first connecting element in the first vertebra and mating of the docking element with the first connecting element, the feature is visible outside skin of the patient to indicate a subcutaneous orientation of the first slot portion.

2. The system of claim 1, wherein the intervening element comprises a portion of the side wall.

3. The system of claim 2, wherein the feature comprises a portal formed in the side wall, discretely from the first slot portion.

4. The system of claim 1, further comprising an insertion tool securable to a rod, the insertion tool comprising a handle configured to facilitate manual guidance of a leading end of the rod through the first slot portion.

5. The system of claim 1, further comprising a second cannula configured to mate with a second connecting element implantable in a second vertebra of the spine, and a third cannula configured to mate with a third connecting element implantable in a third vertebra of the spine, wherein the first, second, and third cannulas cooperate to facilitate attachment of a rod to the first, second, and third connecting elements to restrict relative motion of the first, second, and third vertebrae.

6. The system of claim 5, wherein the first, second, and third cannulas cooperate to facilitate percutaneous attachment of the rod to the first, second, and third connecting elements.

7. The system of claim 1, wherein the first connecting element comprises a pedicle screw implantable in a pedicle of the first vertebra, and a cage polyaxially movable with respect to the pedicle screw.

8. The system of claim 1, wherein the first cannula comprises an adjustable length.

9. The system of claim 1, wherein the docking element is configured to permit alignment of the first and second slots with a rod seat in the first connecting element so as to facilitate passage of a portion of the rod from the slots into the rod seat.

10. The system of claim 1, wherein the feature comprises an opening configured to receive the spinal fusion rod therethrough.

11. The system of claim 1, wherein the docking element is configured to be secured to the first connecting element by rotating the docking element with respect to the first connecting element.

12. The system of claim 11, wherein the docking element is configured to be secured to the first connecting element by rotating the docking element with respect to the first connecting element about the central axis of the first cannula.

13. The system of claim 11, wherein the docking element is integrally formed on the first cannula.

14. The system of claim 13, wherein the docking element is a slot in the first cannula.

15. The system of claim 13, wherein the docking element is configured to mate with the first connecting element by engaging the docking element with an engagement portion of the first connecting element and subsequently moving the docking element towards the first connecting element substantially along the central axis of the first cannula.

16. The system of claim 15, wherein the docking element is configured to be secured to the first connecting element by rotating the docking element with respect to the first connecting element subsequent to mating the docking element with the first connecting element.

17. The system of claim 1, wherein the first cannula comprises a first component and a second component discrete from the first component, the first and second components providing the first component when assembled together.

18. The system of claim 17, wherein the first and second components are aligned with the central axis of the first cannula, the first and second components being at least partially spaced apart along the central axis to provide the first cannula.

19. A system for providing access to a spine of a patient, the system comprising:
   a first connecting element implantable in a first vertebra of the spine; and
   a first cannula comprising a proximal end and a distal end insertable into the patient proximate the spine, the first cannula having a longitudinal axis extending between the proximal and distal ends, wherein the distal end is shaped to mate with the first connecting element, the first cannula further comprising a first slot extending between the distal and proximal ends along the longitudinal axis, and a second slot extending between the distal and proximal ends along the longitudinal axis;
   wherein the first cannula comprises an inner component and an outer component, a portion of the outer component having a stop surface extending transverse to the longitudinal axis, wherein the outer component is movable distally along the inner component until the stop surface contacts a skin surface of the patient to stop further distal movement of the outer component;
   wherein the inner component includes a docking element at a distal end thereof, the docking element being shaped to mate with the first connecting element, the docking element being configured to be secured to the first connecting element by rotating the inner component with respect to the first connecting element;
   wherein the first and second slots are arranged diametrically opposed to one another to permit passage of a rod through the first cannula along a direction transverse to the longitudinal axis.

20. The system of claim 19, wherein the first connecting element comprises a pedicle screw.

21. The system of claim 20, wherein the first cannula defines a channel extending along the longitudinal axis between the proximal and distal ends of the first cannula, and wherein the distal end of the first cannula is shaped to mate with the pedicle screw such that the pedicle screw defines a terminus of the channel.

22. The system of claim 19, wherein the inner component includes two elongated pieces defining the first and second slots therebetween.

23. The system of claim 19, wherein the portion of the outer component having the stop surface is a side portal extending from an outer surface of the outer component.

* * * * *